United States Patent [19]

Bedell et al.

[11] Patent Number: 4,908,676
[45] Date of Patent: Mar. 13, 1990

[54] SENSORS FOR DISSOLVED SUBSTANCES IN FLUIDS

[75] Inventors: Glenn W. Bedell; Benjamin Greene; Marion Davis, all of Las Cruces; Floyd J. Abbott, Hobbs, all of N. Mex.

[73] Assignee: Bio-Recovery Systems, Inc., Las Cruces, N. Mex.

[21] Appl. No.: 135,126

[22] Filed: Dec. 18, 1987

[51] Int. Cl.$^4$ .................. G01N 21/47; G01N 21/59; G01N 21/64; G01N 21/85
[52] U.S. Cl. .................. 356/72; 73/61.1 C; 250/565; 250/573; 250/574; 250/576; 356/318; 356/433; 356/440; 356/448
[58] Field of Search .................. 356/72, 408, 410, 411, 356/414, 420, 425, 432-437, 440, 417, 317, 318, 402, 409, 448; 250/343, 373, 564, 565, 573, 574, 576; 73/23.1, 61.1 C

[56] References Cited

U.S. PATENT DOCUMENTS

| Re. 30,983 | 6/1982 | Stookey . | |
|---|---|---|---|
| 2,979,066 | 4/1961 | Christie | 356/410 |
| 3,095,382 | 6/1963 | Hach . | |
| 3,104,160 | 9/1983 | Geld et al. . | |
| 3,506,403 | 4/1970 | Fryer et al. . | |
| 3,558,277 | 1/1971 | Laman et al. . | |
| 3,663,823 | 5/1972 | Ohlin et al. | 250/565 |
| 3,730,688 | 5/1973 | Schmitt et al. . | |
| 3,748,096 | 6/1973 | Schmitt et al. . | |
| 3,816,075 | 6/1974 | Lambert . | |
| 3,836,331 | 9/1974 | Stookey . | |
| 3,843,325 | 10/1974 | Schmitt et al. . | |
| 4,102,179 | 7/1978 | Snell | 73/61.1 C |
| 4,268,269 | 5/1981 | Proudfoot . | |
| 4,286,965 | 9/1981 | Van Humbeeck et al. . | |
| 4,375,163 | 3/1983 | Yang | 73/61.1 C |
| 4,396,718 | 8/1983 | Proudfoot . | |
| 4,407,962 | 10/1983 | Tobacco et al. . | |
| 4,414,842 | 11/1983 | Small et al. . | |
| 4,448,889 | 5/1984 | Neri et al. . | |
| 4,472,354 | 9/1984 | Passell et al. . | |
| 4,529,708 | 6/1985 | Stephens . | |
| 4,545,957 | 10/1985 | Van Humbeeck et al. . | |
| 4,556,538 | 12/1985 | Matsushita et al. . | |
| 4,567,753 | 2/1986 | Miller, Jr. et al. . | |
| 4,590,424 | 5/1986 | Girot et al. . | |
| 4,629,705 | 12/1986 | Cortes et al. . | |
| 4,652,530 | 3/1987 | Rothman et al. . | |
| 4,672,322 | 6/1987 | Gratteau et al. . | |
| 4,678,338 | 7/1987 | Kitta et al. | 356/420 |
| 4,679,428 | 7/1987 | Miller, Jr. et al. . | |
| 4,690,902 | 9/1987 | Bitsch . | |
| 4,747,686 | 5/1988 | Sato | 356/72 |

FOREIGN PATENT DOCUMENTS 138441 7/1985 Japan .................. 356/436

OTHER PUBLICATIONS

Pump-Colorimeter Copper Analyzer, Model 61700 Hach Co., 1983, 1984.

Primary Examiner—F. L. Evans
Attorney, Agent, or Firm—Skjerven, Morrill, MacPherson, Franklin & Friel

[57] ABSTRACT

The present invention comprises a simple multi-purpose on-line system for monitoring the concentration and/or the total amount of an organic analyte species or inorganic analyte species in an aqueous solution. The on-line detection system comprises a detection column and a sensor mounted around the detection column. The sensor consists of an electromagnetic radiation source (typically a light source) and an appropriate detector for the electromagnetic radiation. The response from the detector drives an electric circuit, which provides a signal to a recorder as well as a means to trip an alarm system and/or a process system.

80 Claims, 7 Drawing Sheets

SENSORS FOR DISSOLVED SUBSTANCES IN FLUIDS

BACKGROUND OF THE INVENTION

1. Field of the Invention

This invention relates generally to the measurement of dissolved substances in water and more specifically to an on-line sensor for monitoring the concentration of dissolved substances in an aqueous solution and for determining the total amount of a dissolved substance in an aqueous solution during a given time interval.

2. Description of Prior Art

Removal and recovery of heavy metals from industrial effluents and mining process streams as well as the detection of other organic and inorganic substances in other fluid streams is becoming increasingly more important. Several prior art techniques exist for monitoring the concentration of either organic or inorganic ions in fluids, but each of these methods has several drawbacks in an on-line industrial setting.

Liquid column chromatography used in conjunction with photometric detection has been used for detection of inorganic ions and organic ions which absorb light. Typically, in liquid column chromatography, separation of the ions in the fluid stream is accomplished using a stationary adsorbent material in a column and a mobile liquid, the eluent, which flows through the column. The sample from the fluid stream, containing the ions of interest, must be such that each of the components of the sample are free to move about in the eluent and freely interchange between the eluent and the stationary adsorbent material When the sample is introduced to the column, different ion species in the sample have different retention times (i.e., are held different times) within the column. Accordingly, the ion species having the shortest retention time flows through the column first and the ion species having the longest retention time leaves the column last. The other ion species in the sample flow through with retention times between these extremes. Therefore, photometric measurement of the light absorbed by the eluent stream as it leaves the chromatographic column and calibration of the light absorption properties of specific ions in the effluent makes it possible to detect the ions in the sample. The primary purpose of liquid column chromatography is to separate and determine the concentration of each ion species in the fluid stream.

If the ions of interest are not light absorbing, another prior art technique, indirect photometric chromatography, may be used. A system for indirect photometric chromatography is shown in FIG. 1. In this method, a sample containing the ions of interest, which are not light absorbing, an eluent having counter-ions and displacing ions, and a stationary adsorbent bed are also used. The displacing ions of the eluent are ions which interact with the stationary absorbent bed, and are ions which can be detected using photometric monitoring. The counter-ions in the eluent are generically the counter-ions to the light absorbing displacing eluent ions. Since the counter-ions do not interact with the stationary adsorbent bed, the concentration of counter-ions in the eluent is fixed. However, either a sample ion or a displacing eluent ion may be associated with a counter-ion.

Initially, the eluent 20 is pumped from the reservoir 22 through the column 10 and the light absorption properties of the effluent from column 10, i.e., the flow stream from the exit of column 10, are determined by photometer 12.

To measure the concentration of the different ions in the sample, the constant eluent flow is maintained through the column 10 but the sample is injected into the eluent through the sample injection valve 18. The sample ions are retarded by the chromatographic column, as previously described. Further, since the concentration of counter-ions is fixed, the appearance of the sample ions in the effluent from column 10 must be accompanied by an equivalent change in the concentration of displacing ions. Thus, when transparent sample ions, or sample ions of lesser absorbance than the displacing ions, reach the photometer 12 a characteristic dip is measured in the effluent absorbance. Hence, the eluent is selected not only for its optical absorbance characteristics, but also for its ability to elute sample ions within practical times.

For a more detailed discussion of indirect ion chromatography, see H. Small and T. Miller, U.S. Pat. No. 4,414,842 issued Nov. 15, 1983; H. Cortes and T. Stevens, U.S. Pat. No. 4,629,705 issued Dec. 16, 1986; T. Miller and Z. Iskandarani, U.S. Pat. No. 4,567,753 issued Feb. 4, 1986; and T. Miller and Z. Iskandarani, U.S. Pat. No. 4,679,428 issued July 14, 1987.

Another approach to ion chromatography uses a high sensitivity conductivity detector which replaces the photometric detector at the base of the chromatographic column. See, for example, J. Gratteau, et al., U.S. Pat. No. 4,672,322 issued June 9, 1987. Instead of measuring the light propagation properties of the effluent, the conductivity technique measures the electrical conductivity of the effluent, which is then used to ascertain the ion content of the sample.

In each of the prior art methods of liquid chromatography, the column is used as a separation means, i.e., as a means for separating the different ion species in the sample, and the ion species and quantities of each ion species in the fluid sample are determined by photometric analysis of the effluent from the chromatographic column. These column chromatographic methods are not practical for on-line sensors and the photometric measurements are subject to interference between different species of ions contained in the sample which have similar retention times in the chromatographic column. Further, these methods require injection of a sample and then waiting for the chromatographic column to separate the different ion species in time so that the concentration of each ion species in the sample can be determined by photometrically monitoring the effluent from the column. None of the methods would function adequately if a continuous stream of sample were provided to the chromatographic column.

In another prior art method using chromatographic columns, Proudfoot, in U.S. Pat. No. 4,396,718 and U.S. Pat. No. 4,268,269, teaches a two step method for detection of triazoles in an aqueous solution. A separation step removes the triazoles from the aqueous solution by adsorption onto a molecular resin. Next, an eluting solvent is passed through the molecular resin containing the previously adsorbed triazole. The eluting solvent desorbs the triazoles and the eluate from the column is essentially free from impurities which would interfere with the quantification of the amount of triazole.

In the quantification step, the eluate containing the triazole is passed through a column containing a cation exchange resin to which is bound a metal ion, wherein the triazole is strongly bound to the surface of the resin as a colored metal ion-triazole complex. After removal of uncomplexed metal from the column, the size and color of complexed metal-triazole bands formed on the column are visually compared with a known standard to determine the concentration of triazoles. This method is impractical for on-line monitoring because a visual measurement is necessary for quantification. Further, since the triazole is strongly bound to the surface of the resin as a colored metal iontriazole complex, the triazoles can not be easily stripped from the column and the column reused for the next measurement.

Other prior art methods use colorimetric techniques to detect ions in an aqueous solution For example, Rothman et al., U.S. Pat. No. 4,652,530, teach a method for a colorimetric determination of isothiazolones in a fluid stream. The isothiazolones are first concentrated on a nonpolar adsorbent. The isothiazolones are stripped from the adsorbent and a reagent is used to break the aromatic ring of the isothiazolones. Then, another reagent is added to produce a colored complex. A conventional colorimetric analysis of the colored complex is used to determine the concentration of the isothiazolones.

Vanhumbeeck et al., in U.S. Pat. No. 4,545,957 and U.S. Pat. No. 4,286,965, teach a method for identifying the absolute value of copper ion concentration in a fluid stream wherein discontinuous samples are taken from the stream, processed, and then colorimetrically analyzed. Laman et al., U.S. Pat. No. 3,558,277, teach a similar method for detecting biodegradable organics in aqueous solution in which the fluid stream is first mixed with a material to precipitate metals from the stream. The stream is filtered to remove the precipitate and then mixed with a permanganate solution and heated for 30–40 minutes. The solution is then diluted and colorimetrically analyzed Each of the prior art systems suffers from several deficiencies which make on-line monitoring of ions in an aqueous solution impractical. The liquid chromatographic equipment is complex and expensive. Chromatographic methods are primarily designed to distinguish multiple ions and the concentration of each ion Chromatographic methods are not generally suitable for either continuous monitoring or monitoring the amount of ion in a process stream during a specified time.

The prior art automated colorimetric methods rely upon an expensive colorimeter to analyze the final product The colorimetric equipment is not a compact self-contained unit that is easily installed in an on-line industrial setting

SUMMARY

In accordance with the present invention a simple multipurpose on-line system is presented for monitoring the concentration and/or the total amount of an organic analyte species or inorganic analyte species in an aqueous solution. The system is compact, self-contained and functions in any setting where it is necessary to monitor the analyte concentration in a stream flow.

In one embodiment of the on-line analyte detection system, a sensor is mounted around a detection column. The sensor consists of a light source and an appropriate detector for the light source. The response from the light detector drives an electric circuit, which provides a signal to a recorder as well as a means to trip an alarm system and/or to activate a process system when the analyte concentration in a process stream either drops below, or increases above a predetermined level.

The sensor is capable of detecting a change in a reflected, transmitted or emitted light caused by the presence of analyte in the detection column. As used herein, analyte refers to the species of interest (whether it is ionized or not) in the process stream. If the analyte has light absorption, transmission, reflection or emission properties that can be detected by the sensor, then a side stream from the process stream containing the analyte is passed through the detection column and is observed directly. The on-line analyte detection system is calibrated by passing streams with known, but different, concentrations of the analyte, which bound the concentrations of the analyte expected in the process stream, through the detection column and the response of the sensor is calibrated so that a selected output signal is generated by an electric circuit, coupled to the sensor, when the analyte in the process stream exceeds a specified concentration.

If the analyte does not have the necessary optical properties, or if it is desired to measure the total amount of analyte in a process stream in a given time period, the detection column is packed with an adsorbent so that as the side stream flows through the detection column, the adsorption of the analyte species of interest in the side stream flow forms a complex on the adsorbent which has light absorption, transmission, reflection, or emission properties that are detectable by the sensor. The accumulation of the analyte on the adsorbent removes the analyte from the side stream and effectively concentrates the analyte so that its presence is easily detected by the sensor. Also, the complex formed on the adsorbent may have a significantly different extinction coefficient than the analyte itself. Accordingly, the formation of the complex on the adsorbent enhances the capability of detecting analyte in the process stream.

Unlike the prior art, where the adsorbent column was used to separate different analyte species so that different analytes appear in the effluent from the column at different times, in accordance with this invention, a boundary layer is created in the detection column packed with adsorbent by the accumulation of the analyte in the side stream on the adsorbent. The boundary layer moves down the detection column with time. The sensor detects when the boundary layer reaches a given point on the detection column, and the time taken for analyte to reach this point is a measure of the concentration of the analyte in the side stream. The higher the concentration of analyte in the stream, the shorter the time taken for the boundary layer to reach the position of the sensor on the detection column. Thus, the more concentrated the analyte in the process stream, the faster the boundary layer formed by the analyte on the adsorbent in the detection column appears to move down the column. If the sensor is placed at a certain position on the column, then the time that is required for the boundary layer to reach the sensor defines the concentration of the analyte in the process stream.

Again, to calibrate the on-line analyte detection system, streams with known but different concentrations of the analyte are passed through the detection column and the time required for the boundary layer to reach the position of the sensor is measured, or alternatively the time required for the boundary layer to reach various positions on the detection column is recorded.

The on-line analyte detection system can be used to determine when the analyte concentration in a process stream either drops below, or increases above a predetermined level. If the analyte concentration in a process stream drops below a predetermined level, then the boundary layer formed by the adsorption of the analyte on the adsorbent in the detection column will not reach the photodetection system in the prescribed time. In this case the control system can be used to activate a switch governing the flow of reagents into a process stream so that the analyte concentration of interest is increased. After the time period of interest, the on-line analyte detection system is taken off-line and the adsorbent in the detection column is stripped of the adsorbed analyte, i.e., the on-line analyte detection system is rejuvenated so that it may be used again, and the system is placed back in service.

To detect when the analyte concentration in a process stream increases above a predetermined level, the sensor is placed on the detection column so that if the analyte concentration in the process stream is less than the specified amount, the boundary layer will not reach the sensor within the prescribed time interval. The sensor will never detect analyte accumulation during the prescribed time interval so long as the analyte remains at the desired concentration. Again, after the prescribed time interval, the column is taken off-line and the adsorbent is stripped of the adsorbed analyte and the detector is placed back in service. If on the other hand, the analyte increases in concentration such that in the prescribed time the boundary layer reaches the sensor, an alarm or chemical adjustment system is activated.

These features make the on-line analyte detection system useful for monitoring wastewater treatment, because the system can be used to monitor analyte concentrations at various points in a water treatment operation. The detection system is capable of either alerting an operator when chemical adjustments are needed in the process stream, or automatically activating the chemical adjust system if it is needed. By placing the detection system at the point at which wastewater is discharged to a sewer, the system functions as an alert system when analyte concentrations are in violation of the fluid discharge limits.

As an additional feature, the detection system can be adapted to measure the total amounts of analyte which have passed a point in a given time. This allows industries, which pretreat waste water prior to discharge, to maintain adequate records for environmental regulatory agencies. This is essential, since federal discharge limits for analytes are set not only for instantaneous values but also for daily and monthly averages.

Similarly, the detection system of this invention may be used in any industrial setting where on-line monitoring is beneficial, or where the total amount of analyte which has passed a point at a given time on a daily, weekly or monthly basis, or where the concentration of the analyte in a process stream must be monitored. Analytes in either organic or inorganic process streams may be detected using this invention.

TERMS

Throughout this specification terms particular to the field of this invention will be used. The definitions of these terms follow.

"Adsorbent"- While this invention will be described in conjunction with the use of adsorbent, it is important to note that the concept of adsorbent includes the use of a material which will retard the migration of the analyte through the sample column 103 (FIGS. 3a and 3b) thereby allowing the concentration of analyte in column 103 to build up above its normal level. Such a build up will make possible the detection of analyte in column 103 and thus serves the same function as though an adsorbent material was present in column 103. Molecular sieves, gel permeation polymers, exclusion polymers, hydrophobic polymers and other materials used in chromatographic separations are materials that perform such a function.

"Adsorption"- the taking up by physical or chemical forces of the molecules or ions of dissolved substances by the surfaces of the solids with which the molecules or ions of dissolved substances are in contact.

"Analyte"- the dissolved substance in a process stream, or reaction products derived from the dissolved substance in a process stream, the concentration or total amount of which is of interest.

"Effluent"- the fluid which results at the exit of a column from passing fluids through the medium in the column.

"Eluate"- an effluent containing a formerly adsorbed substance which results from passing eluent through an adsorbent containing column.

"Eluent"- a fluid passed through an adsorbent containing column to remove adsorbed species.

"Extinction coefficient"- the absorbance of light traveling through a one centimeter path length of a solution containing the analyte at a one molar(M) concentration. This definition follows from the definition of absorbance which is a manifestation of Beer's law. The absorbance is defined by the following equation:

$$A = \epsilon c d$$

where
- $A$ = absorbance,
- $\epsilon$ = molar extinction coefficient,
- $c$ = concentration of analyte in molarity (moles/liter); and
- $d$ = path length (cm) through which light travels in the sample.

DETAILED DESCRIPTION OF THE INVENTION

Figure 1:
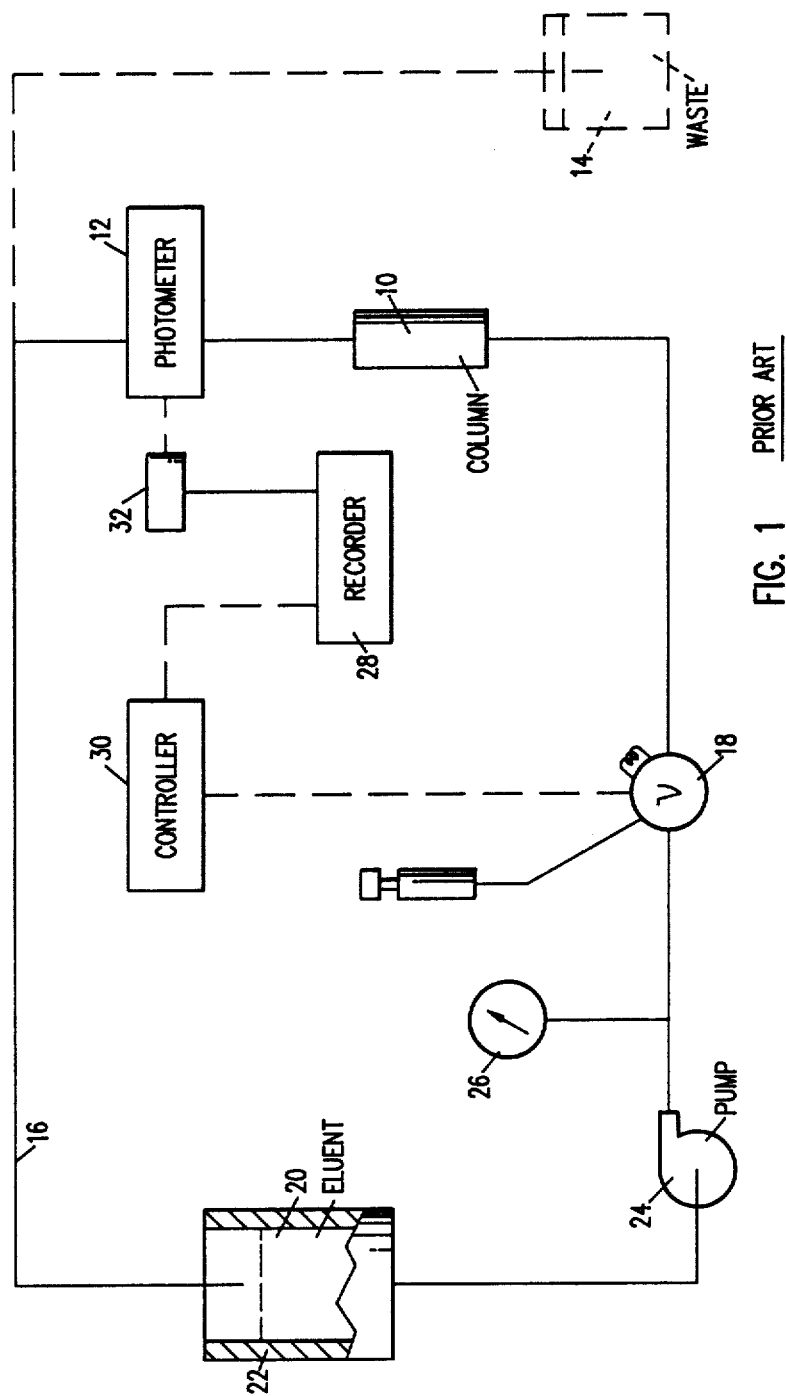
FIG. 1 is a prior art system for indirect photometric chromatography.
Figure 2:
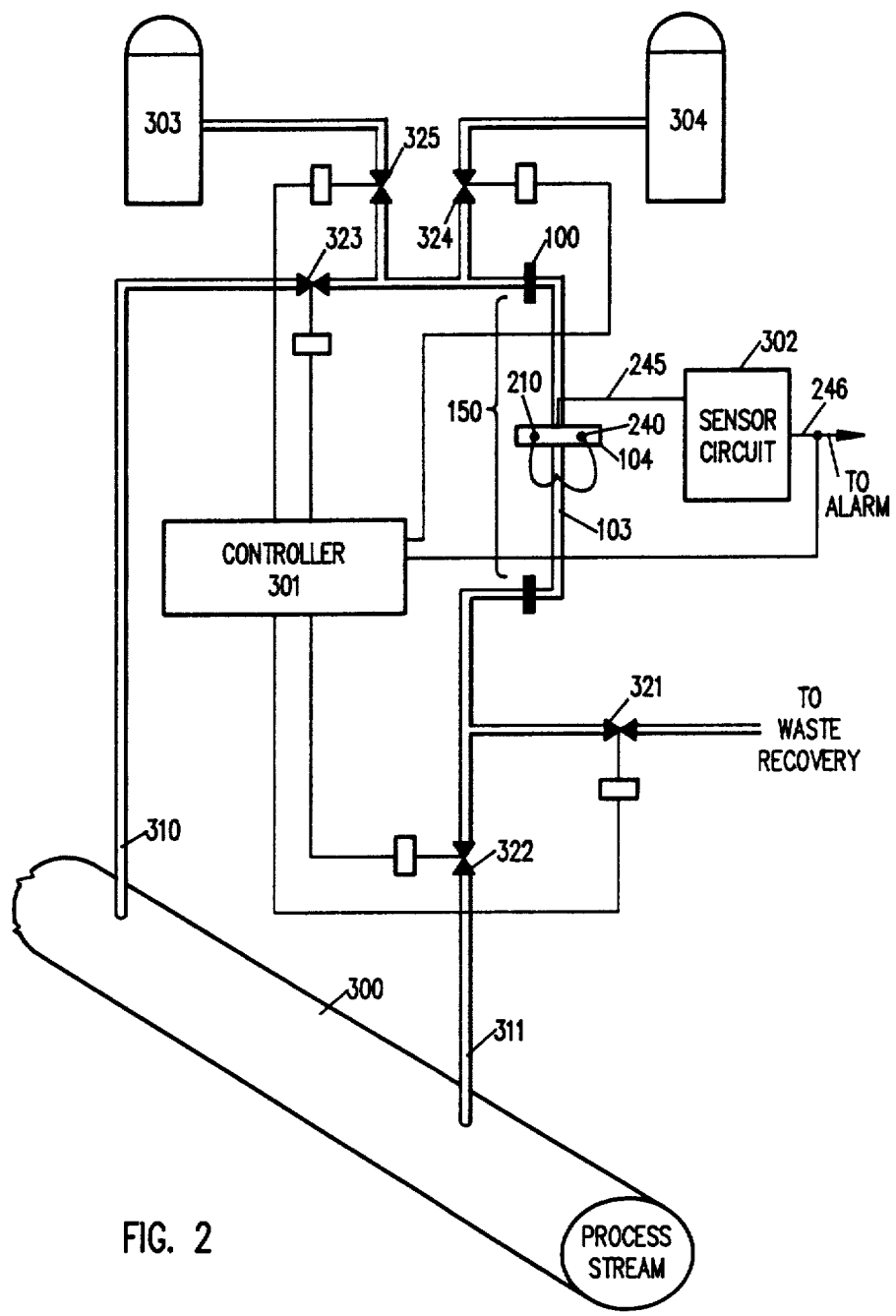
FIG. 2 illustrates the on-line analyte detection system of this invention.

The on-line analyte detection system (analyte detector) of this invention is illustrated in FIG. 2. As used herein, analyte refers to the dissolved species of interest (whether it is ionized or not) or a reaction product of the dissolved species of interest in the process stream. The process stream containing the analyte of interest is flowing through the pipe 300. A side stream is extracted from the process stream through the line 310. The side stream flows from the pipe 300 through a first motor operated valve 323 to the inlet 100 of the analyte detector 150. The flow rate of the side stream can be set at any desired rate, but a convenient rate is less than one milliliter per minute, and if the process stream in pipe 300 is not pressurized, a small pump (not shown) is incorporated in line 310 to drive the side stream to inlet 100. The side stream flows through the detection column 103 of analyte detector 150 and the sensor 104, mounted around the detection column 103, detects the presence of the analyte as will be described later. The side stream leaves detection column 103 and enters line 311 where the stream flows through a second motor operated valve 322 and then returns to the process stream in pipe 300.

The sensor 104 contains a light source 210, typically a light emitting diode (LED), and a light detector 240, typically a phototransistor, and the detection column 103 is a transparent tube. In one embodiment (not shown) the LED 210 and light detector 240 are contained 180° apart in sensor 104. Hence, the detector 240 measures the light from LED 210 transmitted through the contents of detection column 103. In the embodiment in FIG. 2, the LED 210 and the light detector 240 are located in the sensor 104 so that the light from LED 210 is reflected by the contents of detection column 103 into light detector 240. In yet another embodiment, LED 210 and light detector 240 are located such that the LED 210 causes the contents of detection column 103 to fluoresce and light detector 240 measures the fluorescent light.

Accordingly, the optical properties of the analyte and/or the adsorbed analyte define the configuration of the sensor 104 that is used in the on-line analyte detector 150. If the analyte in the process stream has light absorption, transmission, or emission properties that can be detected by sensor 104, the side stream is simply passed directly through detection column 103 and the optical properties of the analyte are detected by the sensor 104.

If the analyte does not have the necessary optical properties, or if it is desired to measure the total amount of analyte in the process stream in a given time period, detection column 103 is packed with an adsorbent so that as the side stream from line 310 flows through detection column 103, the adsorption of the analyte species of interest in the side stream flow forms a complex on the adsorbent. The formation of the complex on the adsorbent removes the analyte from the side stream and effectively concentrates the analyte so that its presence is easily detected by sensor 104. Also, the complex formed on the adsorbent may have a significantly different extinction coefficient from the analyte itself. Accordingly, the formation of the complex on the adsorbent enhances the capability of detecting the presence of the analyte in the process stream.

The controller 301, in FIG. 2, sequences the operation of the on-line analyte detector 150. Initially, the controller 301 holds closed the motor operated value 324 to a first reagent tank 304, the motor operated valve 325 to a second reagent tank 303 containing an eluent, and the motor operated valve 321 to the waste recovery system. The controller 301 activates a timer, which determines the sampling period, i.e., the prescribed time interval, of analyte detector 150, and opens valves 323, 322 so that the side stream starts to flow through on-line analyte detector 150. While motor operated valves are use in this embodiment, any valve, which can be remotely controlled, can be used in the system shown in FIG. 2.

Assume for this example that the detection column 103 contains an adsorbent which reflects light from LED 210 to photodetector 240 and so initially the signal provided to line 245, which connects photodetector 240 to the sensor circuit 302, is first a constant value. The sensor circuit 302 does not energize the output line 246 to controller 301, and to an alarm (not shown) for the first constant value signal.

As the side stream flows from line 310 through valve 323 and into detection column 103, a boundary layer is created by the accumulation of the analyte in the side stream on the adsorbent in detection column 103. The boundary layer moves down detection column 103 with time. The time taken for the boundary layer to move from the top of detection column 103, i.e., the end of column 103 closest to inlet 100, to the position of sensor 104 on the detection column 103 is a measure of the concentration of the analyte in the process stream in pipe 300. The higher the concentration of analyte in the process stream in pipe 300, the faster the boundary layer will reach the position of sensor 104 on detection column 103. Accordingly, sensor 104 is positioned on detection column 103 so that if the analyte concentration in the process stream in pipe 300 is less than a specified amount, the boundary layer will not reach sensor 104 within the sampling period which is programmed into controller 301.

The sensor 104 will never detect the boundary layer of the adsorbed analyte during the sampling period so long as the analyte remains at the desired concentration. After the sampling period, controller 301 closes valves 322 and 323 so that analyte detector 150 is isolated from the process stream in pipe 300, i.e., detector 150 is taken off-line. Next, controller 301 opens valve 325 to eluent reagent tank 303 and valve 321 to the waste recovery system. An eluent from reagent tank 303 flows through detection column 103 to the waste recovery system. The eluent strips the adsorbed analyte from the adsorbent in detection column 103 and returns the adsorbent to substantially its original state. After the adsorbent is stripped, controller 301 places the analyte detector 150 back on-line as previously described.

If the analyte in the process stream in pipe 300 exceeds the desired concentration during the sampling period, then the boundary layer moves more rapidly down detection column 103 and reaches the position of the sensor 104 within the sampling period. When the boundary layer reaches sensor 104, the adsorbed analyte absorbs light from LED 210 which reduces the amount of light reflected and consequently the output signal from photodetector 240 on line 245 to sensor circuit 302 decreases.

In response to the signal on line 245, sensor circuit 302 energizes the alarm to alert personnel of the process stream deviation and energizes a circuit in the controller which takes analyte detector 150 off-line prior to the end of the sampling period. The controller 310 then aligns the eluent reagent tank 303 with detection column 103 as previously described.

Some analytes do not have an absorption or emission spectrum which is detectable, other analytes are not conveniently adsorbed on any matrix even though the analyte has acceptable optical properties. In these cases the analyte detector 150 utilizes either a reaction product of the analyte wherein the reaction product has acceptable spectroscopic characteristics, or the reaction product is better adsorbed on the adsorbent in detection column 103. In these instances, controller 301 is set so that motor operated valve 324 is opened and the reagent in reagent tank 304 is metered into the side stream in line 310 when valves 322 or 321 and 323 are open. The interaction of the reagent with the analyte in the side stream produces a product which has detectable spectroscopic properties and/or which is adsorbed on the adsorbent in detection column 103. The sensor 104 is set as previously described and the operation of analyte detector 150 is also as previously described.

Figure 3C:
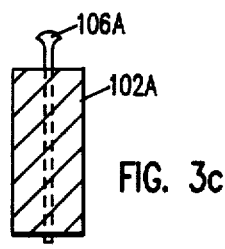
FIG. 3c illustrates the disperser screen of the on-line analyte detector.
Figure 3A:
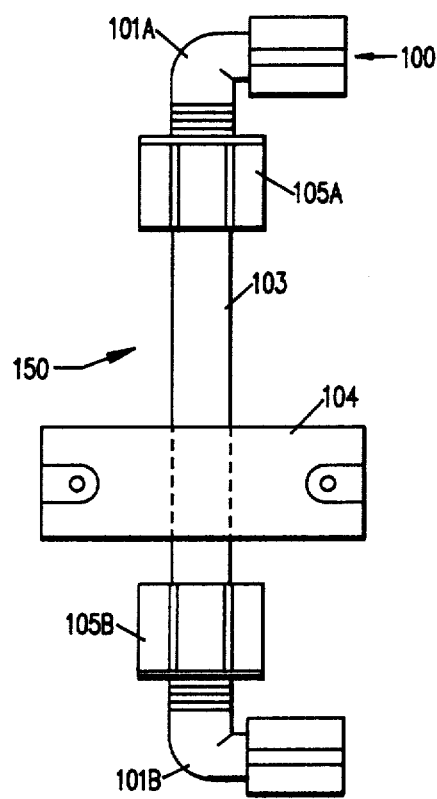
FIG. 3a illustrates the assembled on-line analyte detector of this invention.
Figure 3B:
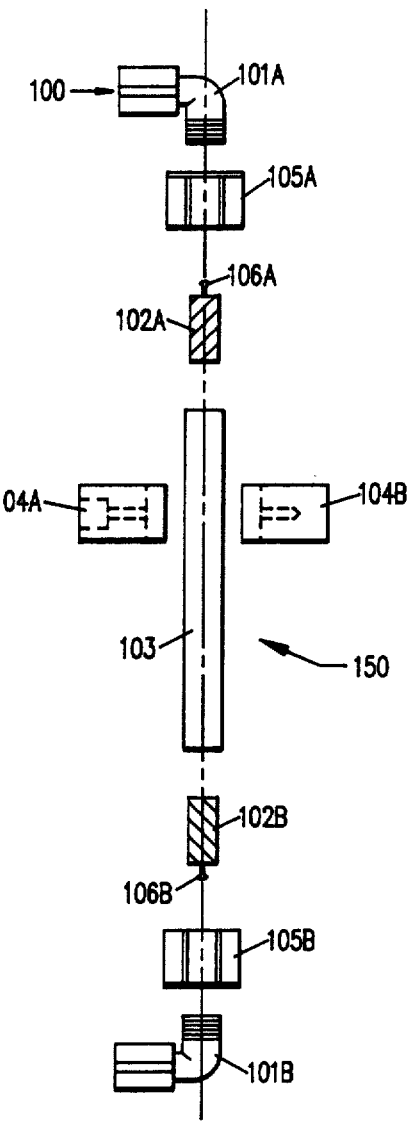
FIG. 3b illustrates the components of the on-line analyte detector.

Of importance, the analyte detector 150, shown in FIGS. 3a and 3b and particularly detection column 103 and sensor 104 are placed in an opaque container to prevent external light from effecting the readings of photodetector 240 contained within sensor 104. Interestingly, more than one sensor 104-detection column 103 combination can be contained within a given opaque structure thus allowing one opaque structure to be used with a plurality of analyte detectors. Thus, a plurality of side streams can be passed through one opaque box. In this embodiment, a corresponding plurality of flow meters are mounted on the outside of the box thereby to allow the flow through each of the side streams to be measured and regulated. In one embodiment, two side streams were passed through the opaque box which contained two analyte detectors. Two flow meters, mounted on the outside of the box, allowed the process flow in each side stream to be monitored and regulated. Hence, the flow into each analyte detector was monitored and regulated.

The on-line analyte detection system 150 (analyte detector) of this invention is illustrated in FIG. 3a in the assembled configuration, while FIG. 3b illustrates the individual components in detection system 150. In one embodiment, inlet 100 is ⅜ inch tubing with a ¼ inch female NPT 90° fitting 101A (FIG. 3b), which is connected to a tube fitting 105A that is bored out to 13/32 of an inch to accommodate the ten millimeter outside diameter tube which comprises the detection column 103 of analyte detector 150. Of course, piping with other dimensions can be used, but as is explained later, the size of detection column 103 affects the performance of analyte detector 150.

As the side stream flow passes through the 90° fitting 101A and the tube fitting 105A (FIG. 3b), the flow encounters a 51 mesh polypropylene disperser screen 102A, typically 1 1/16 ×3 7/8 inches, which is wrapped around a polypropylene 1/8 ×1 inch rod 106A (FIG. 3c). While a 90° fitting 101A is used in this embodiment, other fittings with other angles may of course be used.

The preparation and installation of the disperser screen is as follows. Polypropylene screen of 51 mesh (obtained from McMaster-Carr No. 9275T19) was cut in approximately 4 ½ inch lengths with a width of 1 1/16 inch for the upper disperser screen 102A and with a width of 1 ¼ inch for the lower disperser screen 102B. Each screen was then hot air welded to a ⅛ inch polypropylene rod 106A, 106B. After wrapping the screens around the rod, excess screen was trimmed to allow insertion of the rod with the screen into a ten millimeter outside diameter tube. The disperser screen 102A filters particles from the flow stream and equalizes the flow distribution so that the flow is uniformly distributed as it enters the top of the pyrex detection column 103, which has a 7 millimeter inside diameter and a five inch length.

The material from which detection column 103 is fabricated can be any material such as glass, pyrex, quartz, or plastic which is capable of transmitting light or other electromagnetic radiation at the frequencies of interest. However, the material for detection column 103 must be selected such that the wavelength of the light source 210 going into the column or the wavelength of the light emitted from the material in the column detected by light detector 240 passes through the material without significant attenuation.

If the detection of the analyte species requires an adsorbent, the column 103 is packed with the adsorbent using standard chromatographic techniques. To prepare a resin for use as the adsorbent in column 103 (FIGS. 3a and 3b, a cation chelating ion exchange resin (SR5 obtained from Sybron) is described as an illustration. The resin (SR5) was washed with de-ionized water and then dried in air and sieved to select particles with a size of 41 through 50 mesh. The 41 through 50 mesh size particles were then spread on a white background and any black or dark brown beads were removed. Beads which were light brown or lighter in color were retained because they turn lighter after immersion in water and therefore are suitable for use in column 103 of this invention. The above is one example of adsorbent preparation. Other adsorbents of course can be used for other applications and the invention is not limited to the use of this particular adsorbent. These other adsorbents would be packed in column 103 using standard chromatographic techniques.

After the side stream flow passes through detection column 103, the flow encounters another polypropylene disperser screen 102B, similar to the screen 102A described above, before entering a second tube fitting 105B and a second ⅜ inch tube with a ¼ inch female NPT 90° fitting 101B. The side stream flow is returned to the process stream after leaving the analyte detector as illustrated in FIG. 2.

The sensor 104 in FIG. 3a, is mounted on the detection column at a specified location, as described below, to detect the analyte species in the side stream.

The layout of the on-line analyte detector, as shown in FIGS. 3a, 3b, and 3c permits easy coupling to any process stream and unlike the prior art systems, the on-line analyte detector 150 is easily accommodated in any industrial or similar setting. Further, the detector 150 is comprised of readily available components and the detection system requires no special heating or electronics to operate.

Figure 4:
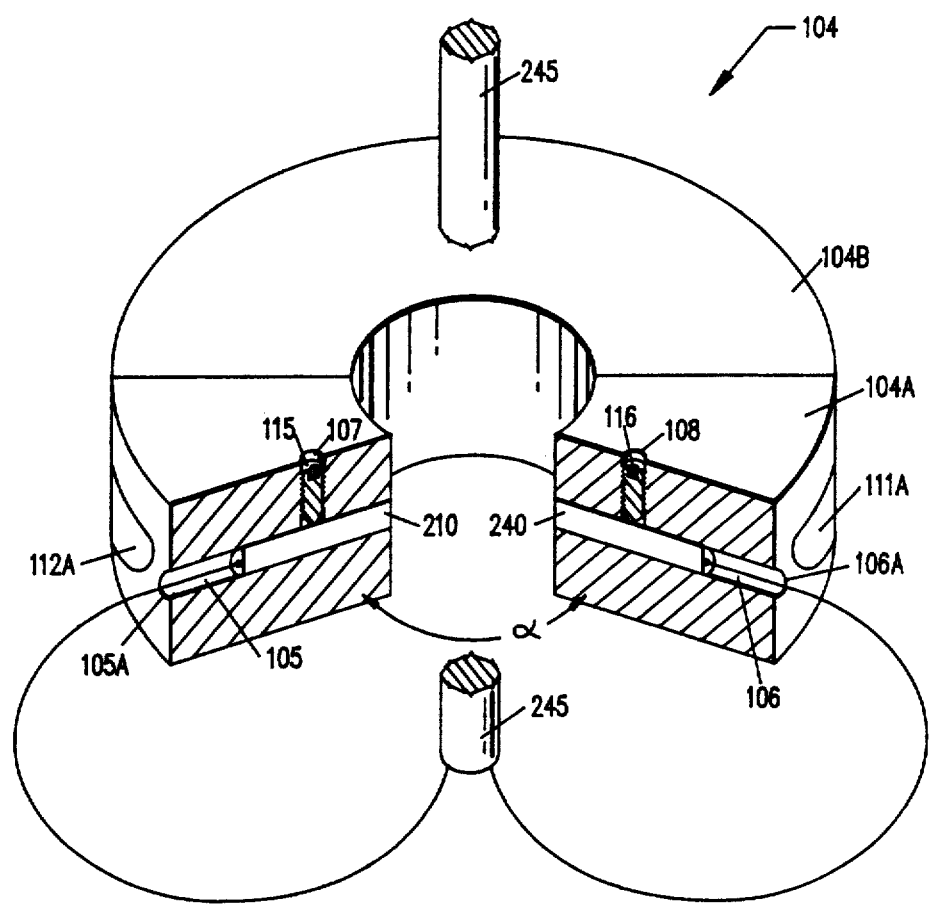
FIG. 4 is a geometric view of the sensor of the on-line analyte detector.
Figure 5A:
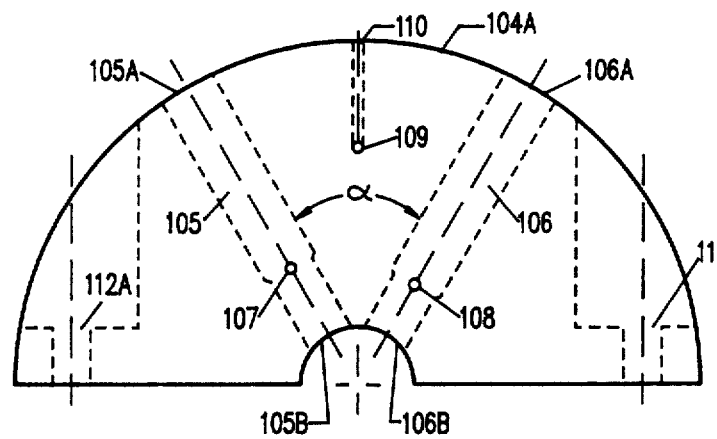
FIG. 5a illustrates a top view of the second half of the sensor collar for reflective extinction operation of the on-line analyte detection system.
Figure 5B:
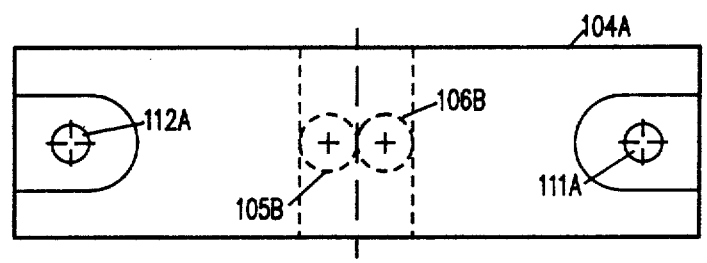
FIG. 5b illustrates a side view of first half of the sensor collar for reflective extinction operation of the on-line analyte detection system.

The sensor 104 in FIG. 2 and FIG. 3a of the analyte detector is comprised of a collar 104, having two halves 104A, 104B, as illustrated in FIG. 3b which fit around the detection column 103. The collar 104, as illustrated in FIG. 4, contains a light source 210 and a light detector 240 which comprise the active components of the sensor. In one embodiment, the sensor body 104, the collar, is a right circular cylinder which is divided into two halves. A first half 104A of the collar is illustrated in top and side view in FIGS. 5a and 5b and the second half 104B of the collar is illustrated in top and side view in FIGS. 6a and 6b. The two-inch diameter right circular cylinder comprising the collar has a ten millimeter hole drilled through its centerline to accommodate detection column 103. As shown in FIGS. 5a, and 5b two holes 105, 106 are drilled at the midpoint of the height of the right circular cylinder from the outside surface of the cylinder 105A, 106A through to the inner surface 105B, 106B formed by the hole for detection column 103. The two holes 105, 106 are drilled such that they form with each other an angle $\alpha$. As described below, the angle $\alpha$ between holes 105, 106, i.e., the angle between the light source 210 and the photodetector 240 in FIG. 4, is selected to optimize the sensitivity of the sensor 104 for a broad range of applications.

The light source 210, typically a light emitting diode, is placed in hole 105 and secured by an allen set screw 115 inserted in the tapped hole 107 as shown in FIG. 4. Similarly, the photodetector 240, typically a phototransistor, is securely held in hole 106 by an allen set screw 116 inserted through the tapped hole 108 also shown in FIG. 4. The light source 210 and photodetector 240 are mounted such that they do not extend past the inner surface of collar 104A, but yet they are mounted as close as possible to detection column 103. Thus, in FIG. 4, light source 210 and photodetector 240 are shown aligned with the inner surface of collar 104A. In FIG. 5b, the tapped holes 107, 108 for the allen set screws 115, 116 are not shown in the front view of collar 104A for clarity.

In another embodiment, light source 210 and photodetector 240 are mounted outside the body of sensor 104. In this embodiment, a first fiber optic cable is secured in hole 105 and a second fiber optic cable is secured in hole 106. The cables are secured in holes 105, 106 so that they are flush with the inner surface 105B, 106B of the sensor body formed by the hole for detection column 103. One of the fiber optic cables is connected to light source 210 outside the sensor body and the other fiber optic cable is connected to photodetector 240 which now is also outside the sensor body. This embodiment permits the use of larger, and in certain instances more sensitive, light sources and photodetectors.

A third hole 109 shown in FIG. 5a is drilled completely through the collar half 104A from the top of the cylinder to the bottom of the cylinder and another hole 110, shown in FIG. 5a, is drilled and tapped from the outside surface of collar half 104A at 90° to hole 109 so that a electrical nylon set screw can be screwed tightly against the electrical line 245 that runs through hole 109 to the photodetector 240 and the light source 210. In FIG. 5b the tapped hole 110 and hole 109 are also not shown in the front view of the collar 104A for clarity.

Figure 6A:
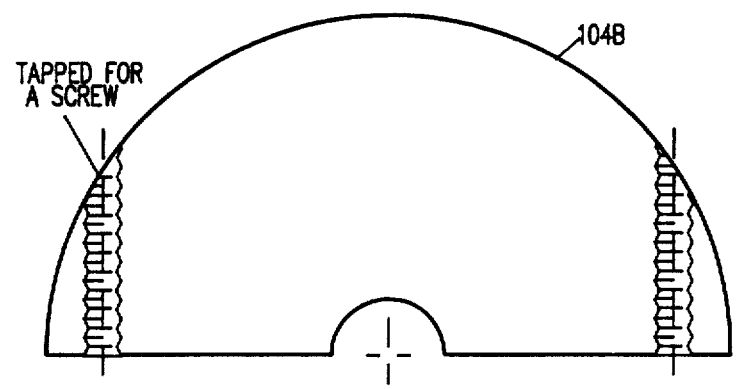
FIG. 6a illustrates the top view of second half of the sensor collar for reflective extinction operation of the on-line analyte detection system.
Figure 6B:
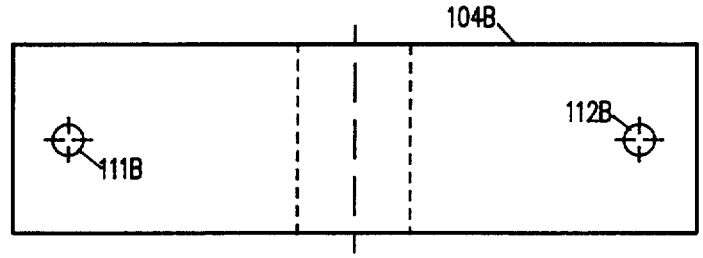
FIG. 6b illustrates the side view of second half of the sensor collar for reflective extinction operation of the on-line analyte detection system.

The second half of the collar 104B, illustrated in top and side views in FIG. 6a and 6b, has two holes 111B, 112B drilled and tapped so that screws inserted through holes 111A, 112A in collar 104A may be tightened, and accordingly the sensor positioned and held at any elevation on detection column 103. Hence, as is explained in more detail later, the sensor 104 can be positioned on the detection column 103 such that the analyte detector 150 in FIG. 2 monitors the analyte concentration in the process stream for any time period of interest. The closer the sensor 104 is located to the inlet 100 in FIG. 2, the shorter the time period required for the adsorbed analyte boundary layer to reach the sensor 104.

The sensor 104 operates in one of three modes. In the first mode, called the reflective extinction mode, the light reflected by the adsorbent in detection column 103 is measured When the adsorbed analyte reaches the light source, the adsorbed analyte absorbs some of the light and hence the reflected light decreases. Thus, in this mode, a light source, the LED 210, is placed at a suitable angle $\alpha$ with respect to a compatible light sensor, i.e. photodetector 240, within the collar as shown in FIG. 4 For reflected light measurement, the angle $\alpha$ could range between 0° and 90°. If the angle $\alpha$ were 0°, there would be a minimum of reflected light from the surface of the glass detection column 103. As the angle $\alpha$ is increased, more light is reflected from the surface of the glass detection column 103 which means less light reaches the adsorbent in the detection column and hence the sensitivity is decreased. An angle of $\alpha = 60°$ has been empirically shown to provide a good range of sensitivity for a broad range of applications in the reflective extinction mode.

For analytes such as copper(II), nickel(II), and chromium(III), which are adsorbed on an adsorbent such as an ion exchange resin, a red light emitting diode (LED) provides light of the proper wave length and a red light sensitive Darlington phototransistor is the photodetector. For other analytes, such as zinc(II) or cobalt(II), the di-$\beta$-napthylthiocarbazone complexes of zinc(II) or cobalt(II) can be detected by a green LED and a green light sensitive photoconductive cell in sensor 104 for the reflective extinction mode. Likewise magnesium(II) and calcium(II) complexes with Erichrome Black B, as described later, can be detected using a green LED and a green light sensitive photoconductive cell in sensor 104 for the reflective extinction mode. Use of a yellow LED and a yellow light sensitive phototransistor can be used for the detection of methylthymol blue complexes of lead(II) or zinc(II). A near infrared LED with appropriate phototransistor can be used for the detection of vanadium(III). An ultraviolet lamp with appropriate photodetector can be used for chromium(VI) and a wide variety of transition metal ion complexes.

In a second mode of operation, called the transmission mode, sensor 104 is designed to measure light transmitted through the contents of detection column 103 (FIG. 3a) and this is accomplished by a second embodiment of sensor 104 wherein the angle $\alpha$ between light source 210 and the photodetector 240 is 180° (i.e., the light source 210 is opposite the photodetector 240).

The third mode of operation, called the fluorescence mode, is for analytes which fluoresce when excited by a light source. In the fluorescence mode, a light source, LED 210, is again placed at a suitable angle $\alpha$ to a compatible light sensor, photodetector 240, within the collar as shown in FIG. 4. The angle $\alpha$ can be any angle between 0° and 180°, but an angle of 60° optimizes the sensitivity with respect to the amount of reflected and scattered light vs. the amount of fluorescent light detected.

If the detector is operating in the fluorescence mode without an adsorbent in the column, the inner filter effect, well known in fluorescence spectroscopy, may become important. This means that higher concentrations of the analyte may actually result in a decrease in sensitivity of light which is detected. This occurs because the sample itself absorbs the excitation energy at high concentrations. Accordingly, this inhibits an accurate determination of analyte concentration for high concentrations. On the other hand, when an adsorbent is in the column and the detector is operating in the fluorescence mode only those molecules which are near the surface of the column upon which light is impinging are excited. Therefore, the inner filter effect is minimized at all concentrations of the analyte. In contrast to most fluorescence spectrometers where the light source and the detector are separated at an angle of 90°, the most sensitive operation of detector 104 in this application is closer to an angle of $\alpha = 60°$.

As is apparent from the equation for absorbance given above under the definition of the extinction coefficient, if an analyte has a small extinction coefficient, the absorbance can be increased by increasing the path length for a clear liquid with an analyte contained therein or by increasing the molarity concentration of the analyte. The molar concentration is increased by concentrating the analyte on the adsorbent in the detection column. Both of these changes increase the amount of light absorbed and thus make possible the measurement of analyte by measuring the light intensity from the sample. By increasing the values of the concentration c and the path length d in the absorbance equation, the absorbance of a given analyte is made less sensitive to errors and the uncertainty in the measurement is decreased from that which would be present if only small differences in the absorbance of the sample were being measured. In the following description, the operation of the on-line analyte detection system in the reflective extinction mode is described. The principles of operation of the on-line analyte detection system in the transmission mode and fluorescence mode will be apparent in view of this description.

Preconcentration of the analyte is required if the concentration of the analyte in the process stream is low and/or if the analyte has a small extinction coefficient. Preconcentration is accomplished by passing the side stream in line 310 (FIG. 2) containing the analyte through detection column 103 which contains an adsorbent for the analyte. A variety of chromatographic materials can be used as the analyte adsorbent in column 103. The choice of the adsorbent is dependent upon the properties of the analyte. Adsorbents include but are not limited to, weak and strong acid cation exchange resins, weak and strong base anion exchange resins, chelating ion exchange resins, molecular sieve or exclusion polymers, hydrophobic polymers, hydrophilic polymers, affinity chromatographic matrices, biological materials and inorganic polymers such as zeolites, silica or alumina. The only restrictions on the adsorbent are that it concentrate the analyte and that the light absorbing properties of the adsorbent not interfere with the detection of the analyte. The only restriction on the analyte is that the adsorbed analyte or a reaction product derived therefrom must have optical properties such that it absorbs and/or emits light of a measurable wave length.

As the side stream containing the analyte passes through the analyte detector 150 (FIG. 2) the analyte first accumulates on the adsorbent in column 103 closest to the inlet 100. As the adsorbent in column 103 near inlet 100 becomes saturated with analyte, the analyte flows past the saturated region of the adsorbent and accumulates on the adsorbent directly adjacent to the saturated adsorbent of the column 103. This gives the appearance of a boundary layer of adsorbed analyte slowly moving down column 103. The more concentrated the analyte in the process stream the faster the adsorbed analyte appears to move down the column 103, assuming that the flow rate of the side stream through column 103 is constant. If sensor 104 is placed at a certain position on detection column 103, then when the boundary layer reaches sensor 104, the boundary layer absorbs light from light source 210 in sensor 104 (FIG. 4) and, consequently, the level of light reflected to the photodetector 240 in sensor 104 decreases. See FIGS. 2 and 4.

Figure 7:
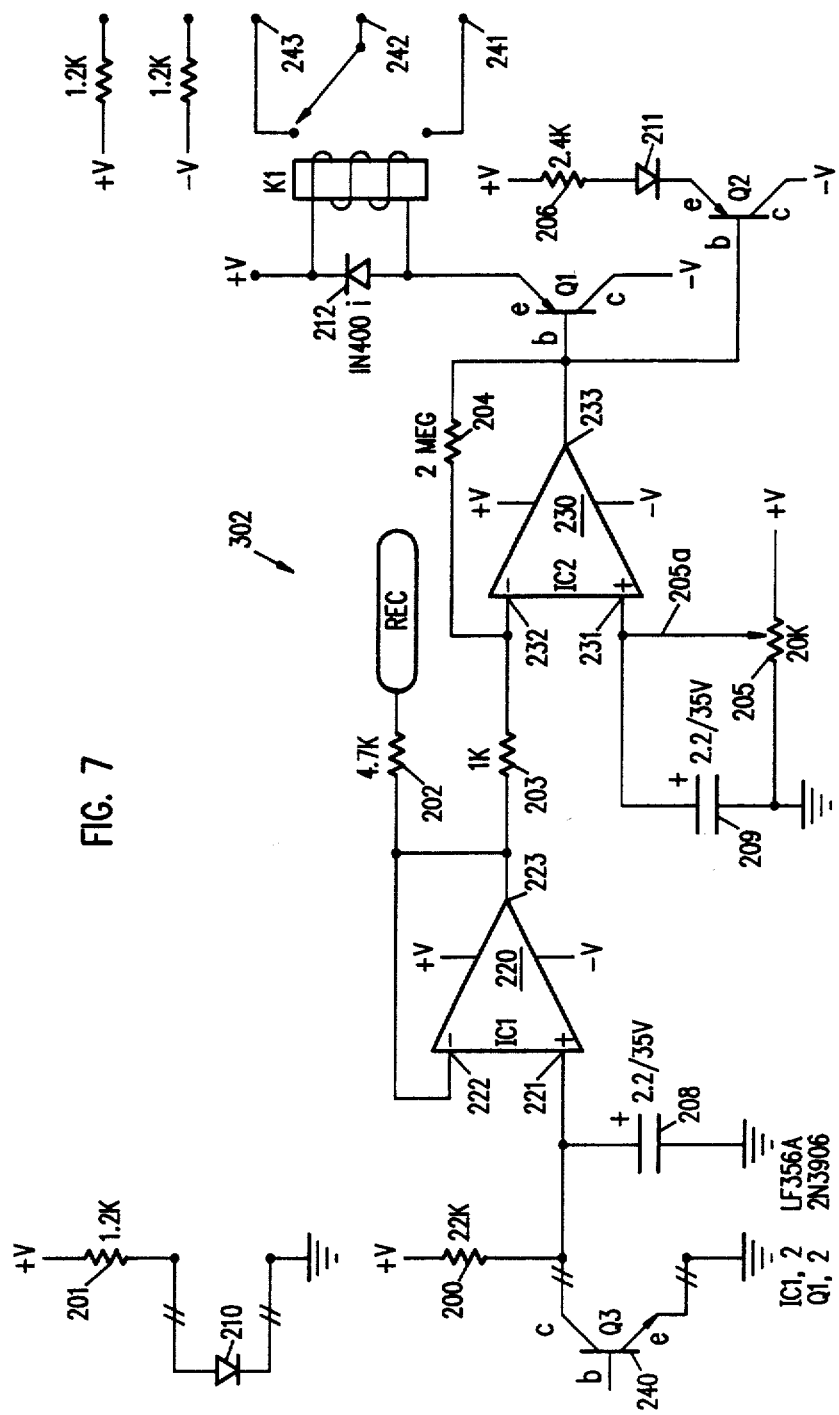
FIG. 7 is a schematic diagram of the sensor circuit in the on-line analyte detection system.

This decrease in the reflected light level is detected by a circuit 302 illustrated in FIG. 7 which includes the photodetector 240, Darlington phototransistor $Q_3$. The circuit 302 in FIG. 7 provides an electrical signal to drive a recorder and to trip an alarm and/or to activate a process system in response to increased or decreased absorption of light by the adsorbed analyte. While the absorption of light by the adsorbed analyte is described in this embodiment, in another embodiment, the adsorbent is pre-coated with a substance which absorbs more light than the adsorbed analyte. Since the analyte has a higher affinity with the adsorbent than the substance coating the adsorbent, the analyte displaces the coating substance on the adsorbent. In certain applications it is not necessary to have a coating substance. That is, if for example a brown resin is used which absorbs light of a particular wavelength, then when an analyte binds to the surface of the resin, the result may be that less light is actually absorbed because more light is reflected by the analyte complex bound to the resin. Accordingly, in either of these cases, the adsorbed analyte increases the light reflected to the photodetector 240. The operation of electric circuit 302 for an increase in reflected light to photodetector 240 will be apparent to one skilled in the art in view of this disclosure.

Referring to FIG. 7, the photodetector 240 is a Darlington phototransistor Q3. In one embodiment, phototransistor Q3 is a red light sensitive G.E. Darlington Photodetector L14F1 and in another a green light sensitive EG&G VACTEC photoconductive cell VT-201. Other types of photodetectors can, of course, be used with appropriate changes in the circuitry. The positive power supply voltage +V (typically 12 volts) is supplied through a first resistor 200 to the collector c of the Darlington phototransistor Q3. In one embodiment, the regulated power supply provides ±12 volts for operation of up to ten sensor circuits 302 and the related light sources. The emitter e of transistor Q3 is connected to ground. Prior to the analyte reaching the sensor, the light from a light emitting diode (LED) 210, having its anode coupled to the positive power supply voltage +V through a resistor 201 and the cathode connected to ground, impinges upon the base b of Darlington phototransistor Q3 and turns on transistor Q3 which conducts a current to ground thereby dropping the voltage on collector c of transistor Q3 from a +V when Q3 is off, to a much lower voltage just above ground when Q3 is saturated. Although LED 210 and transistor Q3, photodetector 240, are shown in FIG. 7, both are physically located in sensor 104 on the detection column 103 as shown in FIG. 2.

A first operational amplifier 220 generates an output signal proportional to the current flow through transistor Q3 because the non-inverting terminal 221 of operational amplifier 220 is connected to the collector c of Darlington phototransistor Q3. The output terminal 223 and the inverting input terminal 222 of the operational amplifier 220 are tied together. Thus, operational amplifier 220 buffers the transistor Q3 from the rest of the sensor circuit. Capacitor 208 is normally charged to +V when transistor Q3 is off but discharges through Q3 when transistor Q3 is on so that capacitor 208 is charged to the voltage on collector c when Q3 is on. Capacitor 208 together with the collector to emitter resistance of transistor Q3 acts as a filter.

The output signal generated by operational amplifier 220 in response to the current flow through Darlington phototransistor Q3 is not only fed back to the inverting input terminal 222 of operational amplifier 220, but also is applied to a first terminal of resistor 202. The resulting signal on the second terminal of the resistor 202 drives a recorder. The size of resistor 202, 4.7K ohms in one embodiment, is selected so that if the recorder connected to resistor 202 short circuits, the sensor circuit 302 is not damaged by excessive current drawn from operational amplifier 220.

The voltage on the output terminal REC applied to the recorder remains constant as long as the light on the base b of transistor Q3 remains substantially constant because the electrolytic capacitor 208, having a positive terminal connected to the non-inverting input terminal 221 of the operational amplifier 220 and a negative terminal connected to ground, filters any noise on the non-inverting terminal 221 of the operational amplifier 220. However, since operational amplifier 220 functions as a voltage follower with a gain of unity, the signal level to the recorder on terminal REC changes when the boundary layer formed by the adsorbed analyte reaches sensor 104 (FIG. 2) and the collector current of Darlington phototransistor Q3 decreases because the light reflected to the base b of Darlington phototransistor Q3 is decreased by the light absorbed by the adsorbed analyte.

The output signal from operational amplifier 220 is also passed through resistor 203 to the inverting terminal 232 of a second operational amplifier 230 and to one terminal of resistor 204. The resistance of resistor 203, 1 K ohm in one embodiment, is selected to achieve feedback stability of operational amplifier 230. The second terminal of feedback resistor 204 is tied to the output terminal 233 of operational amplifier 230. In one embodiment, the resistor 204 is 2 megaohm. While the operational amplifier 230 will work without the feedback path formed by resistor 204, making resistor 204, 2 megaohm, limits the saturation of operational amplifier 230 and causes amplifier 230 to operate with almost an open loop gain.

The non-inverting input terminal 231 of operational amplifier 230 is connected to ground through a second electrolytic capacitor 209 and to the positive power supply voltage +V through an adjustable resistor 205, having a total resistance of 20K ohms in one embodiment. The output signal from operational amplifier 230 in response to the signal from operational amplifier 220 is not only fed back to the inverting input terminal 232 of operational amplifier 230, but also is applied to the base b of PNP transistor Q1 and to the base b of PNP transistor Q2. As described below, prior to the adsorbed analyte reaching the sensor 104 the output signal from the operational amplifier 230 is set at the positive power supply voltage +V so that transistors Q1 and Q2 are off. Accordingly, the relay K1, which is a single pole, double throw relay and has one lead from the coil of the relay connected to the positive power supply voltage +V and the other lead from the coil of the relay connected to the emitter e of transistor Q1, is not energized because transistor Q1 is off and thus is not conducting. Transistor Q1 is effectively an open switch. Similarly, the light emitting diode 211, which is provided to emit light when the adsorbed analyte at the sensor reaches a certain level and which has an anode coupled to the positive power supply voltage +V through resistor 206 and a cathode connected to the emitter e of Q2, is off because the transistor Q2 does not conduct.

The tap on the variable resistor 205 is set so that the input voltage on the non-inverting input lead 231 to operational amplifier 230 is such that the output signal of operational amplifier 230 is the positive supply voltage +V before the adsorbed analyte reaches the sensor 104. However, when the adsorbed analyte reaches sensor 104 in FIG. 2, the light absorption of the adsorbed analyte decreases the light reflected to Darlington phototransistor Q3 as previously explained. Accordingly, the current flow through transistor Q3 decreases, which in turn increases the output signal of operational amplifier 220.

The variable resistor 205 is set such that this increased output signal from the operational amplifier 220 to the inverting terminal 232 of operational amplifier 230 causes the output signal of operational amplifier 230 on lead 233 to change state, i.e. switch from the positive power supply voltage +V to the negative power supply voltage −V. Hence, the location of tap 205a on variable resistor 205 (which functions as a voltage divider) sets the threshold level i.e., the comparison level, of the input signal on inverting input lead 232 where the output signal on lead 233 of operational amplifier 230 changes from the positive power supply voltage +V to the negative power supply voltage −V. The lower the voltage on input lead 232, the less analyte required to trigger this change from positive to negative of the output signal from operation amplifier 230.

Prior to the time when the adsorbed analyte reaches sensor 104, the relay K1 is not conducting, as described above, and the device (for example, a recorder or a CRT) connected to the terminals 242, 243 of relay K1 is enabled. However, when the adsorbed analyte reaches sensor 104 and consequently the output signal of operational amplifier 230 changes state from +V to −V, as described above. The negative output signal turns on both transistors Q1 and Q2. Transistors Q1 and Q2 function as emitter followers. When transistor Q1 turns on, current flows through the coil of relay K1 which is connected such that the device (such as an audible and/or visible alarm, or recorder) connected to the terminals 241, 242 of relay K1 is energized. Similarly, when transistor Q2 turns on, a current flows through the light-emitting diode 211 which indicates that the analyte has reached sensor 104. The diode 212 across the coil of relay K1 is chosen so that when the relay K1 is de-energized the inductive voltage generated across relay K1 is limited and does not harm transistor Q1.

To illustrate the operation of this unique on-line analyte detection system 150, as shown in FIG. 2, assume that a copper ion in the process stream is the analyte and sensor 104 sounds an alarm whenever the copper concentration is above 1 part per million (ppm) in the process stream. A variety of adsorbents can be used in detector column 103 for the detection of the copper ion and for this example a cation exchange resin is used. Cation exchange resins include, but are not limited to, weak acid cation exchange resins, strong acid cation exchange resins, chelating cation exchange resins and biological materials with properties that enable them to function as ion exchange resins. The copper accumulates on the resin as the side stream from the process stream flows through the detection column 103 and produces a blue color which is specific for the copper ion in the process stream in pipe 300.

Figure 8:
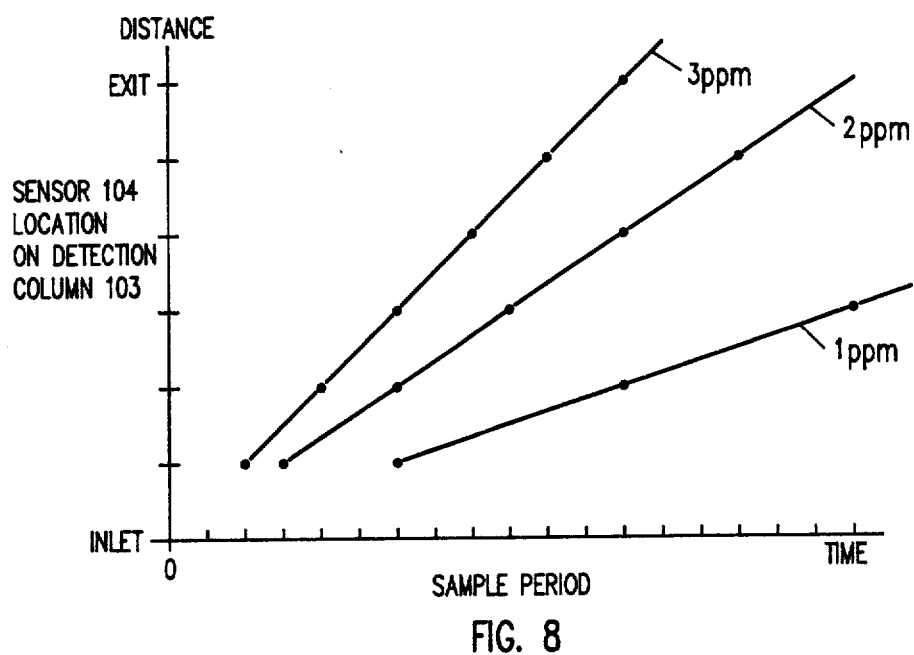
FIG. 8 is a calibration curve for the copper-ion detector.

The sensor 104 has been positioned on column 103 such that for a concentration of 1 ppm, the blue boundary layer formed by adsorbed copper ion takes a specified number of minutes to reach sensor 104. The location on the column for the specified time is determined by the calibration of the sensor. For example, streams with a 1 ppm, a 2 ppm and 3 ppm concentration of copper ions where passed through detection column 103 and the time to reach a specified location on the column recorded. The results were plotted with the locations of the sensor on the ordinate and the time on the abscissa, as shown in FIG. 8. Accordingly, reference to the graph in FIG. 8 defines the location of sensor 104 for a specified time, i.e., sampling period, and the specified 1 ppm concentration.

If the sensor does not trip within the sampling period after the copper ion detection system is activated by controller 301 in FIG. 2 and side stream flow in line 310 is applied to inlet 100 of the detection column 103, the copper concentration in the process stream is less than 1 ppm. In this case, after the sampling period, the on-line copper ion detector is deactivated, i.e. valves 322, 323 are closed, and a stream of an eluent (in this case dilute acid) from tank 303 is directed through the detection column 103 to strip the adsorbed copper from the cation exchange resin.

The detector is then placed back into operation for the sampling period and if the alarm is not tripped within the sampling period, the process is repeated. If during the time interval that the detector is activated the copper concentration increases above the desired 1 ppm limit, then the adsorbed copper band will migrate down the detection column 103 to sensor 104 within the sampling period.

As described previously, when the blue band reaches sensor 104, the blue band absorbs the light from the LED 210 in sensor 104, which in turn decreases the amount of reflected light to the base b of Darlington phototransistor Q3. Accordingly, the output signal from operational amplifier 220, which senses the reduced current flow through transistor Q3, increases. At some point in time in response to the increased output signal from operational amplifier 220 the output signal of the operational amplifier 230 switches from +V the positive power supply voltage, to −V, the negative power supply voltage. This change in the output signal from operational amplifier 230 turns on transistors Q1 and Q2 which in turn energize the relay K1 and the LED 211, respectively. The energizing of relay K1 closes the circuit between the terminals 241 and 242 to which an alarm is attached. Hence, when the boundary layer reaches sensor 104 the alarm is activated. The alarm and the LED 211, thus, indicate that the concentration of copper in the process stream is greater than 1 ppm.

In another embodiment, a chemical adjustment system for the process stream is connected to terminals 241 and 242 and this system is activated when relay K1 closes. The LED 211, which also is activated, provides an alternative means to verify that the sensor has detected the adsorbed analyte indicating that the analyte concentration in the process stream exceeds the desired level and that the chemical adjustment system should be activated.

This demonstrates the unique ability of the on-line analyte detector. The detector samples and thus monitors on a continuous basis the flow through the detection column 103 and provides a means for activating an alarm and/or a chemical adjustment system. Unlike prior art chromatographic methods which analyzed the effluent from a column, the sensor 104 of this invention is on the column. Further, the analyte detection system operates continuously and periodically by accumulating adsorbed analyte on a detection column and determining whether the adsorbed analyte reaches a selected position on the column during a selected time period. Then, after the selected period, the adsorbed analyte is stripped from the detection column and the process repeated. The prior art systems used the chromatographic column to retard the arrival of various analyte species in the effluent from the column, and were not capable of continuously monitoring the analyte concentration in the process stream in the manner of this invention. To replicate the monitoring capability of the analyte detection system with the prior art methods, multiple samples would have to be extracted from the process stream over the selected time period. Each sample would then be introduced into a separate chromatographic column and the photometric measurement on the effluent of each column averaged with the results for the other samples taken. This, of course, assumes that the retention time of the analyte in the prior art chromatographic column is significantly less than the selected time period. Accordingly, the detection system of this invention is a significantly more efficient means for making the desired measurements.

The analyte detection system of this invention is simpler and less expensive than the prior art systems, yet the analyte detection system can provide both the analyte concentration in a process stream, as described above, and the total quantity of an analyte in a process stream in a specified period. To determine the total accumulated amount of an analyte in a process stream, the position of the boundary layer on the column is measured at the end of the time frame of interest. This position is then converted to a total amount through calibration of the detector, i.e., streams with known concentrations are passed through the detector for the specified time and the level on the column measured. The specified time and concentration of each calibration run are converted to a total amount of analyte for a specified level on the detection column. Accordingly the measured location on the detection column is easily converted to a total amount of analyte in the process stream.

The sampling period, i.e., the selected time, can be set at any desired time interval. The time interval is governed by the analyte concentration level desired in the process stream and the distance from the top of the detection column 103 that the sensor 104 is positioned.

The positioning of the sensor 104 on the detection column 103 is dependent upon how closely the concentration of the analyte in the process stream is to be monitored. For example, if the sensor 104 is positioned halfway down the detection column 103, the adsorbed analyte band formed on the adsorbent in detection column 103 may take several hours, for example five hours, to move down to the position of the sensor 104. However, for a particular application, five hours may be too long a sample period, because if the analyte concentration increases to 2 ppm, the analyte detector may take as long as 150 minutes to sound an alarm. This means that for over two hours the process stream has continued flowing without the increased analyte concentration being detected.

In instances where this time interval is unacceptable, sensor 104 is moved up on detection column 103, which in turn decreases the time interval for detection. For example, if sensor 104 is moved near the disperser screen closest to the inlet of column 103, then the time interval may be decreased to one hour. Now, if the analyte level increases to 2 ppm, the analyte detector will signal at 30 minutes. If this time interval is still too long, the time interval can be further decreased by increasing the flow of the side stream through detection column 103. Alternatively, the time interval can also be decreased by using a smaller diameter detection column 103. Hence, the response of the analyte detection system is easily adjusted to meet the monitoring requirements for any given process stream, or to provide a measure of the total amount of analyte which has passed a point in the process stream in a given period of time.

In another implementation of the unique on-line analyte detection system, several sensors 104 are positioned on the same detection column 103 so that several different analytes can be monitored simultaneously. For this system, each analyte or reaction product therefrom must have an absorption or emission spectrum, which is separated from that of the other analytes, so that the one analyte does not interfere with the detection of another analyte. The detection column 103 is filled either with a single adsorbent which binds several analytes, or different adsorbents that are layered on top o one another. The sensors 104 are positioned on column 103 with respect to the position where the analyte to be detected by the sensor is first adsorbed in the detection column 103.

The analyte detection system of this invention also provides a means for direct display of analyte concentration in a process stream. In this embodiment, two sensors are stacked on the same detection column. Measurement of the time interval between detection of adsorbed analyte boundary layer by the first sensor and detection of the adsorbed analyte boundary layer at the second sensor in conjunction with the calibration of the sensors provides a direct display of analyte concentration in the process stream.

The calibration of the direct display of analyte concentration is achieved by simply passing different known concentrations of the analyte at constant flow rates through the analyte detection system and measuring the time interval between the detection of the adsorbed analyte at the first sensor and at the second sensor. The higher the concentration of analyte, the faster the adsorbed analyte band moves down detection column 103. Thus, the time intervals measured for known concentrations of analytes to travel between the sensors provides a basis for interpolating or extrapolating from the measured time for an unknown concentration of analyte to activate the second sensor after the first sensor directly into a concentration of this analyte. While the calibration for the direct display of analyte concentration has been described, the calibration of other embodiments of the on-line analyte detection system is accomplished in a similar manner.

In another embodiment with adsorbent in the column, several sensors 104 are stacked on the detection column 103 and the concentration range of an analyte in the process stream is determined by which of the sensor(s) 104 is/are activated in a given time period. For example, assume five sensors are stacked on the column. The first sensor is positioned to detect 1 ppm of analyte in the process stream, the second sensor is positioned to detect 2 ppm of analyte, the third sensor detects 3 ppm of analyte and similarly the fourth and fifth sensors detect 4 ppm of analyte and 5 ppm of analyte respectively, all in the same time interval. In the given time period, the first two sensors have detected adsorbed analyte, but the adsorbed analyte band has not yet moved to the position of the third sensor. This information immediately translates into a concentration range of analyte, e.g., 2-3 ppm.

The intersection of the plot of the time at which each sensor is activated versus sensor number (which represents ppm present in the stream if that sensor has been activated during the fixed time interval) yields directly the ppm of the analyte in the stream. Hence, if the time at which the adsorbed analyte reaches each sensor is recorded, the plot can be used to predict the ppm at the end of the time interval. For example, in FIG. 9, sensor 1 is reached at time $t_1$, sensor 2 at time $t_2$ and sensor 3 at time $t_3$. Drawing a line through the three points shows that at the given time $t_g$ the concentration will be between 3 ppm and 4 ppm. Hence, using this approach not only provides a direct reading at time $t_g$, but also permits prediction of the reading prior to time $t_g$.

Figure 9:
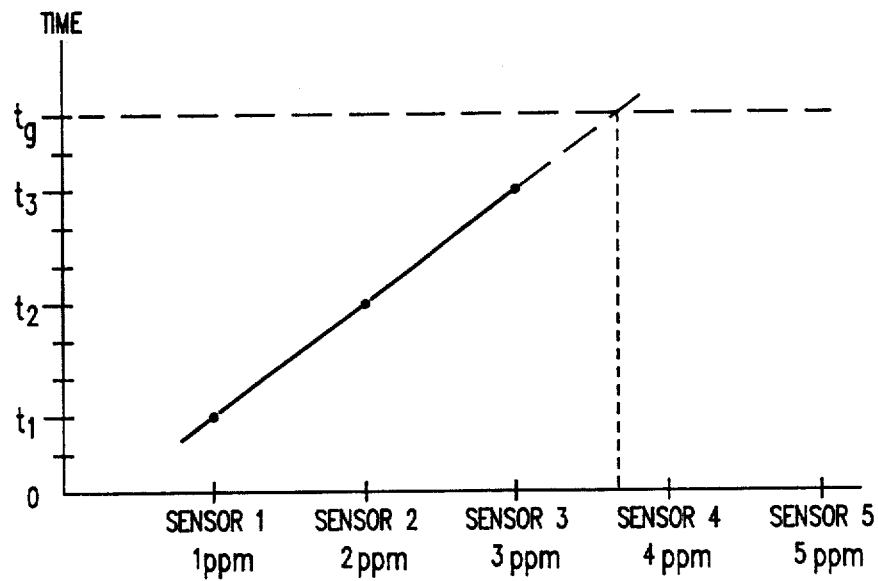
FIG. 9 is a plot illustrating the prediction of the concentration in the process stream using multiple sensors on a single detection column.

FIG. 9 assumes for simplicity that the times of actuation of sensors 1, 2, 3 etc. are linearly proportional to the analyte concentration of the sample stream. Moreover, FIG. 9 assumes that the concentration of the sample stream is essentially constant during the measurement time. Should the concentration of the sample stream vary during the measurement time, then the time to activate a given sensor will be a measure of the average concentration in the sample stream over the time period being measured. Moreover, the ordinate (time axis) is shown to be linear. However, the ordinate does not have to be arranged linearly nor do the locations of the sensors on the abscissa (the X axis) have to be arranged linearly. Rather, the location of the significant times and the locations of the sensors can be varied on each axis to reflect the experimental results necessary to use this figure to predict the concentration of analyte in the sample stream from one or two measurements.

Note that even one measurement can be used to predict the concentration of the analyte in the sample stream by comparing the time at which one sensor is activated to the time $t_g$ at which that sensor would be activated with a known concentration. Also note that while the curve in FIG. 9 may be linear over small ranges, in certain situations the curve may not be linear over larger ranges. The same comment applies to the curves of FIG. 8. While these curves may be linear over small ranges, they likewise may not be linear over larger ranges. Experimental work is required to determine the actual shapes of these curves for given analytes and for given sensor locations.

To calibrate the analyte detection system wherein the analyte has a high extinction coefficient and an adsorbent is not used in detection column 103, flows with known concentrations of the analyte are passed through the detection column 103, and the variable resistor 205, in FIG. 7, is adjusted so that for flow streams having a concentration level greater than the desired level, the relay K1 is energized. For the analyte detection system with a single sensor, flow streams with a known but different concentration of the analyte are passed through the detection column, and for each concentration of the analyte, the voltage output for each concentration is recorded. Thus, a given voltage for the process stream can be directly translated into concentration.

The requirements for a practical on-line analyte detector are that (1) either the analyte have a high enough extinction coefficient to be detected by the sensor if an adsorbent is not used, or the adsorbed analyte on the adsorbent in the detection column produces a concentration of analyte or reaction product derived therefrom such that it can be detected, and (2) the absorption or emission spectrum of the analyte or adsorbed analyte is such that by use of appropriate light sources and photodetectors the analyte is detected without interference from other chemical species.

Some analytes do not have an absorption or emission spectrum which is detectable, other analytes are not conveniently adsorbed on any matrix even though the analyte has acceptable spectroscopic properties. In these cases the detector for the specific analyte utilizes either a reaction product of the analyte wherein the reaction product has acceptable spectroscopic characteristics, or the reaction product is better adsorbed on the adsorbent. In these instances, a reagent, which reacts with the analyte, is metered into the side stream passing through detection column 103. The interaction of the reagent with the analyte in the side stream produces the desired product which is then monitored by the detector system.

Copper(II) ions, nickel(II) ions, chromium(III) ions and chromium(VI) ions are adsorbed on a variety of materials and are detected by the visible absorption bands which are characteristic of each ion. Cadmium(II) ions, Zn(II) ions, Pb(II) ions and Hg(II) ions do not generally have absorption bands in the visible region of the spectrum. However, each of these analytes forms a complex with dithizone which has a unique, intense absorption in the visible region of the spectrum. Thus, in one embodiment dithizone is metered into the column (either with or without an adsorbent), and in another embodiment dithizone is immobilized on a polymer matrix and this polymer matrix with the immobilized dithizone is used as an adsorbent in the detector column.

Calcium(II) ions and Mg(II) ions are not specifically detectable, but after reaction with an indicator reagent, such as Erichrome Black T, the reaction product can be detected. Accordingly, Erichrome Black T is either metered into the side stream or immobilized on a polymer matrix for use in detecting these analytes. Cyanide ions also have no visible adsorption spectrum, but if iron(II) and iron(III) are metered into the stream, an intensely-colored iron cyanide complex is formed. The iron cyanide complex is adsorbed on an anion exchange resin in the detection column.

Iron(II) or iron(III) is detected by metering thiocyanate ions into the side stream to form intensely-colored complexes which are adsorbed on an anion exchange resin. Similarly, thiocyanate and azide ions are detected by metering iron(II) into the side stream.

Amines are detected by reaction with fluorodinitrobenzene followed by adsorption on an ion exchange resin or other resins depending upon the properties of the amine. The dinitrobenzene-amine adduct is an intensely yellow compound. The permanganate ion is intensely colored and is adsorbed on anion exchange resins. Indicators which change colors at specific pH values can be immobilized on a polymer to monitor pH with the detection system of this invention. A number of organic ions or molecules (or reaction products derived therefrom) are intensely colored and can be adsorbed on ion-exchange resins or other adsorbents.

As an example of the above process consider a cyanide ion detector. Iron is metered into the side stream to make $Fe(CN)_6^{-3}$ (ferricyanide ion) which is adsorbed on the anion exchange resin in the detection column 103. The iron is metered into the side stream so that the iron concentration is at least one-sixth the concentration of cyanide in the process stream. Thus, if cyanide ion is to be detected between concentrations of 1–10 ppm (3.8 $\times 10^{-5}$–3.8 $\times 10^{-4}$M), then iron must be metered in so that the concentration of iron going through detection column 103 is at least one-sixth of the maximum cyanide concentration of 3.8 $\times 10^{-4}$M (0.6 $\times 10^{-4}$M) or 3.4 ppm iron. To achieve this level, a concentrated solution of iron is metered through a pump set at a flow rate such that upon introduction of the iron into the side stream the concentration is at least 3.4 ppm. If cyanide is to be detected at higher levels, then correspondingly higher iron concentrations must be metered into the solution. The cyanide detector is calibrated as previously described.

The same approach is taken whenever reagents are to be metered into the side stream to react with the analyte. There is no set concentration or flow rate for each system. Rather, the concentration and flow rates of the metered reagent must be set to accommodate whatever concentration variations of analyte are expected in the process stream.

The sensor of this invention coupled with the sensor circuit is a novel colorimeter. As described, the reflectance, transmittance or fluorescence mode of operation of the sensor provides a colorimeter having a wide range of operable conditions. Further, since the colorimeter is comprised of a detection column, an LED, a photodetector and a sensor circuit, all having readily available standard parts, the colorimeter is not only suitable for operation in an industrial environment but also the colorimeter is considerably cheaper than colorimeters used in the prior art.

The analyte detection system is also a novel application of chromatographic analysis. Unlike the prior art, which analyzed the ion species in the effluent from the chromatographic column and depended upon the separation of ion species by use of a chromatographic column, the present invention uses the chromatographic column as a time dependent means for continuous display of the concentration or total amount of analyte in a process stream. The sensor is accordingly mounted on the column to detect the time when the adsorbed analyte reaches a position on the column which corresponds to a specified or desired level of the analyte in the process stream.

Further, several of the on-line analyte detectors of this invention can be coupled to the same process stream. Then, while one analyte detector is off-line, another can be monitoring the analyte in the process stream. Also, by starting the sensors at alternate times such that two or more sensors are monitoring the analyte in the process stream simultaneously, the readings from the sensors can be used to define differential measurements similar to those when two or more sensors are mounted on the same detection column.

While several embodiments of this invention have been disclosed, it should be understood that the present disclosure merely exemplifies the principles of the invention and is not intended to limit the invention to embodiments illustrated. From the present disclosure, other embodiments and advantages of the invention will be apparent to one skilled in the art.

While an embodiment of this invention has been described using light as the medium for detecting analyte species in column 103, any electromagnetic radiation capable of such use could be used in this invention and the use of the term light is not intended to limit the radiation used to the visible spectrum. Further, while the source of electromagnetic radiation has been described as a light source more particularly as a light emitting diode emitting light having a wavelength selected to be adsorbed by said selected analyte, of course a white light can also be used a the light source. In this situation the portion of the light absorbed by the analyte either alone or as a complex on the adsorbent is a function of the properties of the analyte or the complex. A photodetector is then used to detect the amount of the light absorbed or emitted by the analyte or a complex on the adsorbent. Alternatively, a filter can be used to pass only that portion of the white light spectrum having a wavelength in the area of interest corresponding to the wavelength absorbed by the analyte or the complex on the adsorbent. The amount of light absorbed by the analyte or the complex is then measured using a photodetector sensitive to this wavelength of light. In addition, the same principles would apply to the transmission mode of analyte detection and to the fluorescence mode of analyte detection.

We claim:

1. A method for monitoring the amount of a selected analyte in a process stream comprising:
   withdrawing a side stream from said process stream;
   passing said side stream through a column containing an adsorbent wherein said adsorbent adsorbs said selected analyte and further wherein said adsorbed selected analyte has an extinction coefficient such that said adsorbed selected analyte absorbs detectable electromagnetic energy;
   shining a beam of electromagnetic radiation, having a wavelength absorbed by said adsorbed selected analyte, at a selected location on said column;
   choosing said selected location based upon the amount of said selected analyte and a predetermined sampling period wherein for said predetermined sampling period, said selected location is moved away from an inlet of said column and toward an outlet of said column as said monitored amount of said selected analyte is increased; and
   measuring the level of electromagnetic radiation from said selected location on said column containing said adsorbent as said side stream passes through said column.

2. A method as in claim 1 wherein said beam of electromagnetic radiation comprises light having a wavelength absorbed by said adsorbed selected analyte.

3. A method as in claim 2 wherein said electromagnetic radiation from said selected location on said column is measured by a photodetector.

4. A method as in claim 3 further comprising the step of generating an output signal when said measured level of electromagnetic radiation indicates that the adsorbed selected analyte has reached said selected location.

5. A method as in claim 4 wherein said output signal is generated by an electronic circuit, operatively connected to said photodetector, having a means for comparing a measure of the output signal of said photodetector with a reference signal representative of said amount of said selected analyte, said means for comparing generating an intermediate output signal upon said comparison indicating that the adsorbed selected analyte has reached said selected location; and means, operatively connected to said comparison means, for generating said output signal in response to the intermediate output signal.

6. A method as in claim 5 wherein said reference signal is adjustable so that the output signal is generated for an amount of the selected analyte in said process stream which is different from the amount of the selected analyte at which the output signal is generated before the adjustment.

7. A method as in claim 3 further comprising the step of generating an output signal upon completion of said predetermined sampling period prior to said measured level of electromagnetic radiation indicating that the adsorbed selected analyte had reached said selected location.

8. A method as in claim 3 wherein the level of electromagnetic radiation from said selected location on said column is measured at a selected angle from said beam of light.

9. A method as in claim 8 wherein said measured electromagnetic radiation from said selected location on said column comprises fluorescence emission caused by said absorbed light.

10. A method as in claim 9 wherein said photodetector is sensitive to a wavelength of said fluorescence.

11. A method as in claim 10 wherein said selected angle is about 0° to 180° thereby said photodetector measures said fluorescence.

12. A method as in claim 11 wherein said angle is about 60° thereby to optimize the level of fluorescence detected by said photodetector to a level of reflected and scattered electromagnetic radiation detected by said photodetector.

13. A method as in claim 8 wherein said measured electromagnetic radiation from said selected location on said column comprises reflected light.

14. A method as in claim 13 wherein said photodetector is sensitive to a wavelength of said reflected light.

15. A method as in claim 14 wherein said selected angle is about 0° to 90° thereby said photodetector measures said level of said reflected light.

16. A method as in claim 15 wherein said angle is about 60° thereby providing a good range of sensitivity.

17. A method as in claim 8 wherein said measured electromagnetic radiation from said selected location on said column comprises light transmitted through said selected location on said column wherein the level of light transmitted through said selected portion on said column decreases as the concentration of said selected analyte in said process stream increases.

18. A method as in claim 17 wherein said photodetector is sensitive to a wavelength of said light transmitted through said column.

19. A method as in claim 18 wherein said selected angle is about 180° thereby said photodetector measures said transmitted light.

20. A method as in claim 1 further comprising metering a reagent into the side stream passing through said detection column wherein said reagent interacts with said selected analyte to form a product, said product being adsorbed by said adsorbent, and said adsorbed product functioning as said adsorbed selected analyte.

21. A method as in claim 1 further comprising the steps of:
stopping withdrawal of said side stream upon completion of said predetermined sampling period;
stripping said adsorbed selected analyte from said column so that said column can be reused; and
repeating the method of claim 1.

22. A method for monitoring the amount of a selected analyte in a process stream comprising:
directing a beam of electromagnetic radiation at a selected portion of the process stream, said electromagnetic radiation having a wavelength absorbed by said selected analyte;
measuring the level of electromagnetic radiation from said selected portion of the process stream and producing a first signal in response thereto;
comparing said first signal to a preset electrical reference signal representative of a specified reference concentration of said selected analyte in said process stream; and
generating an output signal when the comparison of said first signal to said preset electrical reference signal indicates that the concentration of said selected analyte in the process stream has changed in relation to said reference concentration.

23. The method of claim 22 wherein said portion of the process stream comprises a selected location on a side stream drawn directly from said process stream.

24. A method as in claim 23 wherein said beam of electromagnetic radiation comprises light having a wavelength absorbed by said selected analyte.

25. A method as in claim 24 wherein said electromagnetic radiation from said selected location is measured by a photodetector.

26. A method as in claim 22 wherein said comparison of said first signal to said preset electrical reference signal is made using an electronic circuit having a means for comparing said first signal to said preset electrical reference signal.

27. A method as in claim 26 wherein said output signal is generated by said electronic circuit when said first signal indicates that the concentration of said selected type of analyte has changed in relation to said reference concentration.

28. A method as in claim 25 further wherein the level of electromagnetic radiation from said selected location is measured at a selected angle from said beam of light.

29. A method as in claim 18 wherein said measured electromagnetic radiation from said selected location comprises light transmitted through said selected location wherein the level of light transmitted through said selected location decreases as the concentration of said selected analyte in said process stream increases.

30. A method as in claim 29 wherein said photodetector is sensitive to a wavelength of said light transmitted through said side stream.

31. A method as in claim 30 wherein said selected angle is about 180° thereby said photodetector measures the level of light transmitted through said side stream.

32. A method as in claim 28 wherein said measured electromagnetic radiation from said selected location comprises fluorescence emission caused by said absorbed light.

33. A method as in claim 32 wherein said photodetector is sensitive to a wavelength of said fluorescence.

34. A method as in claim 47 wherein said selected angle is about 0° to 180° thereby said photodetector measures said fluorescence.

35. A method as in claim 34 wherein said selected angle is about 60° thereby to optimize the level of fluorescence detected by said photodetector to a level of reflected and scattered electromagnetic radiation detected by said photodetector.

36. A method as in claim 22 further comprising metering a reagent into the side stream wherein said reagent interacts with said selected analyte to form a product and said product functions as said selected analyte.

37. A system for monitoring the concentration of a selected analyte in a process stream comprising:
means for directing a beam of electromagnetic radiation at a portion of the process stream, said electromagnetic radiation having a wavelength absorbed by said analyte;
means for measuring electromagnetic radiation from said portion of the process stream and producing a first signal in response thereto;
means for comparing said first signal to a preset electrical reference signal representative of a specified reference concentration of said selected analyte in said process stream; and
means for generating an output signal when the comparison of said first signal to said preset electrical reference signal indicates that the concentration of said selected analyte in the process stream has changed in relation to said reference concentration.

38. The system of claim 37 wherein said portion of the process stream comprises a selected location on a side stream drawn directly from said process stream.

39. A system as in claim 38 wherein said electromagnetic radiation comprises light having a wavelength absorbed by said selected analyte.

40. A system as in claim 39 wherein said means for measuring electromagnetic radiation from said selected location comprises a photodetector.

41. A system in claim 37 wherein said means for comparison of said first signal to said preset electrical reference signal comprises an electronic circuit having a means for comparing said first signal to said preset electrical reference signal.

42. A system as in claim 41 wherein said means for generating an output signal comprises said electronic circuit.

43. A system as in claim 40 wherein said means for measuring electromagnetic radiation further comprises means for measuring electromagnetic radiation from said selected location at a selected angle from said beam of light.

44. A system as in claim 43 wherein said measured electromagnetic radiation from said selected location comprises fluorescence emission caused by said absorbed light.

45. A system as in claim 44 wherein said photodetector is sensitive to a wavelength of said fluorescence.

46. A system as in claim 45 wherein said selected angle is about 0° to 180° thereby said photodetector measures the level of said wavelength of said fluorescence.

47. A system as in claim 46 wherein said selected angle is about 60° thereby to optimize the level of fluorescence detected by said photodetector to a level of reflected and scattered electromagnetic radiation detected by said photodetector.

48. A system as in claim 43 wherein said measured electromagnetic radiation from said selected location comprises light transmitted through said selected location wherein the level of light transmitted through said selected location decreases as the concentration of said selected analyte in said process stream increases.

49. A system as in claim 48 wherein said photodetector is sensitive to a wavelength of said light transmitted through said side stream.

50. A system as in claim 49 wherein said selected angle is about 180° thereby said photodetector measures the level of light transmitted through said selected location.

51. A system as in claim 37 further comprising means for metering a reagent into the side stream wherein said reagent interacts with said selected analyte to form a product and said product functions as said selected analyte.

52. A system for monitoring the amount of a selected analyte in a process stream comprising:
    means for withdrawing a side stream from said process stream;
    a column having an inlet and an outlet, said column containing an adsorbent wherein said adsorbent adsorbs said selected analyte and further wherein said adsorbed selected analyte has an extinction coefficient such that said adsorbed analyte absorbs detectable electromagnetic energy;
    means for passing said side stream through said column;
    a source of electromagnetic radiation having a wavelength absorbed by said adsorbed selected analyte;
    means for positioning said source of electromagnetic radiation so that a beam of electromagnetic radiation from said source is incident upon a selected location on said column, said selected location being any position between said inlet and said outlet of said column; and
    means, operatively mounted on said column, for measuring a level of electromagnetic radiation from said selected location on said column containing said adsorbent as said side stream passes through said column.

53. A system as in claim 52 wherein said source of electromagnetic radiation comprises a light source which produces light having a wavelength absorbed by said adsorbed selected analyte.

54. A system as in claim 53 wherein said means for measuring electromagnetic radiation comprises a photodetector.

55. A system as in claim 54 further comprising means for generating an output signal when said measured level of electromagnetic radiation indicates that the adsorbed selected analyte has reached said selected location.

56. A system as in claim 54 further comprising means for generating an output signal upon completion of a predetermined sampling period prior to said measured level of electromagnetic radiation indicating that the adsorbed selected analyte has reached said selected location.

57. A system as in claim 54 wherein said means for measuring electromagnetic radiation further comprises means for measuring electromagnetic radiation from said selected location at a selected angle from said beam of electromagnetic radiation.

58. A system as in claim 57 wherein said measured electromagnetic radiation comprises fluorescence emission caused by said absorbed light and said photodetector is sensitive to a wavelength of said fluorescence.

59. A system as in claim 58 wherein said selected angle is about 0° to 180° thereby said photodetector measures the level of fluorescence.

60. A system as in claim 59 wherein said angle is about 60° thereby to optimize the level of fluorescence detected by said photodetector to a level of reflected and scattered electromagnetic radiation detected by said photodetector.

61. A system as in claim 57 wherein said measured electromagnetic radiation from said column comprises light reflected from said selected location on said column.

62. A system as in claim 61 wherein said photodetector is sensitive to a wavelength of said reflected light.

63. A system as in claim 62 wherein said selected angle is about 0° to 90° thereby said phtodetector measures the reflected level of light.

64. A system as in claim 63 wherein said angle is about 60° thereby providing a good range of sensitivity.

65. A system as in claim 57 wherein said measured electromagnetic radiation from said selected location on said column comprises light transmitted through said column wherein the level of electromagnetic radiation transmitted through said selected location on said column decreases as the concentration of said selected analyte in said process stream increases.

66. A system as in claim 65 wherein said photodetector is sensitive to a wavelength of said light transmitted through said column.

67. A system as in claim 66 wherein said angle is about 180° thereby said photodetector measures light transmitted through said column.

68. A system as in claim 52 further comprising means for metering a reagent into the side stream passing through said column wherein said reagent interacts with said selected analyte to form a product, said product being adsorbed by said adsorbent, and said adsorbed product functioning as said adsorbed selected analyte.

69. A system as in claim 52 further comprising:
    means, operatively coupled to said passing means, for controlling said passing means so that said side stream is passed through said column for a predetermined period of time wherein for said selected location, said predetermined period of time increases as said amount of said selected analyte in said process stream decreases; and
    means for stripping said adsorbed selected analyte from said adsorbent wherein upon completion of said predetermined period of time, said stripping means removes said adsorbed selected analyte from said adsorbent so that said system can be reused for monitoring the amount of said selected analyte in said process stream.

70. A system as in claim 55 wherein said means for generating an output signal comprises an electronic circuit having a means for comparing a measure of an output signal of said photodetector with a reference signal wherein said output signal is generated when the comparison of said measure of an output signal of said photodetector to said reference signal indicates that the photodetector output signal has changed with respect to the reference signal.

71. A system as in claim 70 wherein said reference signal is adjustable thereby providing a means to measure varied concentrations of selected analytes in said process stream.

72. A colorimeter for comparing the amount of a dissolved substance in a first fluid sample to a selected amount of said dissolved substance in a second fluid sample comprising;
    means for holding said first fluid sample;
    an electromagnetic radiation source producing a beam of radiation having a wavelength absorbed by said dissolved substance, wherein said beam is incident upon said first fluid sample in said means for holding;
    means for detecting electromagnetic radiation from said first fluid sample and for producing an output signal proportional to the intensity of electromagnetic radiation detected;
    means for orienting said source of electromagnetic radiation and said means for detecting said electromagnetic radiation so that said beam of radiation interacts with said first fluid sample in said means for holding said first fluid sample and then electromagnetic radiation from said first fluid sample enters said means for detecting said electromagnetic radiation;
    means for generating a preset reference electrical signal equivalent to said output signal of said means for detecting said electromagnetic radiation when said electromagnetic radiation interacts with said second fluid sample;
    means for comparing said output signal of said means for detecting with said preset reference signal; and
    means for generating an output signal when said output signal of said means for detecting is different than said preset reference signal.

73. A colorimeter as in claim 72 wherein said source of electromagnetic radiation comprises a light-emitting diode.

74. A colorimeter as in claim 73 wherein said means for detecting said electromagnetic radiation comprises a phototransistor.

75. A method for monitoring the amount of a selected analyte in a process stream comprising:
    packing a column, having an inlet and an outlet, with an adsorbent that adsorbs said selected analyte;
    withdrawing a side stream from said process stream;
    passing said side stream through said column so that said selected analyte is first adsorbed by said adsorbent at about the inlet of said column and as said process stream continues to pass through said column the portion of the adsorbent in the column containing adsorbed analyte increases, so that a boundary layer consisting essentially of said adsorbed analyte progresses with time from said said inlet towards said outlet; and
    detecting whether said boundary layer reaches a selected region on said column, said selected region being between said column inlet and said column outlet, thereby determining the amount of said selected analyte in said process stream relative to a predetermined amount of said selected analyte.

76. A method as in claim 75 wherein said step of detecting whether said boundary layer reaches a selected region further comprises:
    positioning a beam of electromagnetic radiation, having a wavelength absorbed by said adsorbed selected analyte, at said selected location on said column; and
    measuring the level of electromagnetic radiation from said selected location on said column as said side stream passes through said column.

77. A system for monitoring the amount of a selected analyte in a process stream comprising:
    means for withdrawing a side stream from said process stream;
    a column having an inlet and an outlet;
    an adsorbent, packed in said column, wherein said adsorbent adsorbs said selected analyte and further wherein said adsorbed selected analyte has an extinction coefficient such that said adsorbed analyte absorbs detectable electromagnetic radiation;
    means for passing said side stream through said column so that said selected analyte is first adsorbed by said adsorbent at about the inlet of said column and as said process stream continues to pass through said column the portion of the adsorbent in the column containing adsorbed analyte increases so that a boundary layer consisting essentially of said adsorbed analyte progresses with time from about said inlet towards said outlet; and
    means for detecting whether said boundary layer reaches a selected region on said column, said selected region being between said column inlet and said column outlet, thereby determining the amount of said selected analyte in said process stream relative to a predetermined amount of said selected analyte.

78. A system as in claim 77 wherein said means for detecting further comprises a source of electromagnetic radiation having a wavelength absorbed by said adsorbed selected analyte.

79. A system as in claim 78 wherein said means for detecting further comprises means for measuring a level of electromagnetic radiation from said selected region on said column as said side stream passes through said column.

80. A system as in claim 79 wherein said means for detecting further comprises means, operatively coupled to said source of electromagnetic radiation and to said measuring means, for positioning said electromagnetic radiation source and said measuring means so that a beam of electromagnetic radiation from said source is incident upon said selected region and said measuring means receives electromagnetic radiation from said selected region on said column.

* * * * *